(12) United States Patent
Moses et al.

(10) Patent No.: US 8,394,096 B2
(45) Date of Patent: *Mar. 12, 2013

(54) OPEN VESSEL SEALING INSTRUMENT WITH CUTTING MECHANISM

(75) Inventors: Michael C. Moses, Boulder, CO (US); Paul R. Romero, Loveland, CO (US); Kristin D. Johnson, Louisville, CO (US); Duane E. Kerr, Berthoud, CO (US); Sean T. Dycus, Broomfield, CO (US)

(73) Assignee: Covidien AG (CH)

( * ) Notice: Subject to any disclaimer, the term of this patent is extended or adjusted under 35 U.S.C. 154(b) by 1 day.

This patent is subject to a terminal disclaimer.

(21) Appl. No.: 13/083,962

(22) Filed: Apr. 11, 2011

(65) Prior Publication Data

US 2011/0238067 A1 Sep. 29, 2011

Related U.S. Application Data

(63) Continuation of application No. 11/546,838, filed on Oct. 12, 2006, now Pat. No. 7,922,718, which is a continuation of application No. 10/991,157, filed on Nov. 17, 2004, now Pat. No. 7,131,970.

(60) Provisional application No. 60/523,387, filed on Nov. 19, 2003.

(51) Int. Cl.
*A61B 18/14* (2006.01)

(52) U.S. Cl. .......................................... 606/51; 606/45

(58) Field of Classification Search ............... 606/45–52
See application file for complete search history.

(56) References Cited

U.S. PATENT DOCUMENTS

| 371,664 | A | 10/1887 | Brannan et al. |
| 702,472 | A | 6/1902 | Pignolet |
| 728,883 | A | 5/1903 | Downes |
| 1,586,645 | A | 6/1926 | Bierman |
| 1,813,902 | A | 7/1931 | Bovie |
| 1,822,330 | A | 9/1931 | Ainslie |
| 1,852,542 | A | 4/1932 | Sovatkin |
| 1,908,201 | A | 5/1933 | Welch et al. |

(Continued)

FOREIGN PATENT DOCUMENTS

| CA | 2 104 423 | 2/1994 |
| CA | 2 520 413 | 3/2007 |

(Continued)

OTHER PUBLICATIONS

U.S. Appl. No. 08/926,869, filed Sep. 10, 1997, James G. Chandler.

(Continued)

*Primary Examiner* — Michael Peffley

(57) ABSTRACT

An open electrosurgical forceps for sealing tissue includes a pair of first and second shaft members each having a jaw member disposed at a distal end thereof. The jaw members are movable from a first position in spaced relation relative to one another to a subsequent position wherein the jaw members cooperate to grasp tissue therebetween. Each of the jaw members includes an electrically conductive sealing plate for communicating electrosurgical energy through tissue held therebetween. At least one of the jaw members includes a cutting slot defined along a length thereof which is dimensioned to reciprocate a cutting instrument therealong for cutting tissue disposed between jaw members. An actuator advances the cutting instrument from a first position wherein the cutting instrument is disposed proximal to tissue held between the jaw members to at least one subsequent position wherein the cutting instrument is disposed distal to tissue held between the jaw members.

18 Claims, 20 Drawing Sheets

U.S. PATENT DOCUMENTS

| | | |
|---|---|---|
| 1,918,889 A | 7/1933 | Bacon |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,113,246 A | 5/1937 | Wappler |
| 2,176,479 A | 10/1939 | Willis |
| 2,305,156 A | 4/1941 | Grubel |
| 2,245,030 A | 6/1941 | Gottesfeld et al. |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,100,489 A | 8/1963 | Bagley |
| 3,372,288 A | 3/1968 | Wigington |
| 3,459,187 A | 8/1969 | Pallotta |
| 3,561,448 A | 2/1971 | Peternel |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,875,945 A | 4/1975 | Friedman |
| 3,897,786 A | 8/1975 | Garnett et al. |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| D249,549 S | 9/1978 | Pike |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,200,104 A | 4/1980 | Harris |
| 4,233,734 A | 11/1980 | Bies |
| 4,236,470 A | 12/1980 | Stenson |
| 4,274,413 A | 6/1981 | Hahn et al. |
| 4,300,564 A | 11/1981 | Furihata |
| 4,306,561 A | 12/1981 | De Medinaceli |
| 4,311,145 A | 1/1982 | Esty et al. |
| D263,020 S | 2/1982 | Rau, III |
| 4,315,510 A | 2/1982 | Kihn |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,513,271 A | 4/1985 | Reisem |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,619,258 A | 10/1986 | Pool |
| 4,624,254 A | 11/1986 | McGarry et al. |
| 4,644,950 A | 2/1987 | Valli |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,674,499 A | 6/1987 | Pao |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| D298,353 S | 11/1988 | Manno |
| D299,413 S | 1/1989 | DeCarolis |
| 4,805,616 A | 2/1989 | Pao |
| 4,827,927 A | 5/1989 | Newton |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,890,610 A | 1/1990 | Kirwan, Sr. et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,122,139 A | 6/1992 | Sutter |
| 5,147,357 A | 9/1992 | Rose et al. |
| 5,151,102 A | 9/1992 | Kamiyama et al. |
| 5,151,978 A | 9/1992 | Bronikowski et al. |
| 5,158,561 A | 10/1992 | Rydell et al. |
| 5,169,396 A | 12/1992 | Dowlatshahi et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,267,998 A | 12/1993 | Hagen |
| 5,269,780 A | 12/1993 | Roos |
| 5,269,804 A | 12/1993 | Bales et al. |
| D343,453 S | 1/1994 | Noda |
| 5,275,615 A | 1/1994 | Rose |
| 5,277,201 A | 1/1994 | Stern |
| 5,281,220 A | 1/1994 | Blake, III |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |

| | | | | | |
|---|---|---|---|---|---|
| 5,308,353 A | 5/1994 | Beurrier | 5,472,442 A | 12/1995 | Klicek |
| 5,308,357 A | 5/1994 | Lichtman | 5,472,443 A | 12/1995 | Cordis et al. |
| 5,313,027 A | 5/1994 | Inoue et al. | 5,476,479 A | 12/1995 | Green et al. |
| 5,314,445 A | 5/1994 | Degwitz et al. | 5,478,351 A | 12/1995 | Meade et al. |
| 5,318,589 A | 6/1994 | Lichtman | 5,480,406 A | 1/1996 | Nolan et al. |
| 5,324,289 A | 6/1994 | Eggers | 5,480,409 A | 1/1996 | Riza |
| D348,930 S | 7/1994 | Olson | 5,482,054 A | 1/1996 | Slater et al. |
| 5,326,806 A | 7/1994 | Yokoshima et al. | 5,484,436 A | 1/1996 | Eggers et al. |
| 5,330,471 A | 7/1994 | Eggers | 5,493,899 A | 2/1996 | Beck et al. |
| 5,330,502 A | 7/1994 | Hassler et al. | 5,496,312 A | 3/1996 | Klicek |
| D349,341 S | 8/1994 | Lichtman et al. | 5,496,317 A | 3/1996 | Goble et al. |
| 5,334,183 A | 8/1994 | Wuchinich | 5,496,347 A | 3/1996 | Hashiguchi et al. |
| 5,334,215 A | 8/1994 | Chen | 5,499,997 A | 3/1996 | Sharpe et al. |
| 5,336,220 A | 8/1994 | Ryan et al. | 5,509,922 A | 4/1996 | Aranyi et al. |
| 5,336,221 A | 8/1994 | Anderson | 5,512,721 A | 4/1996 | Young et al. |
| 5,342,359 A | 8/1994 | Rydell | 5,514,134 A | 5/1996 | Rydell et al. |
| 5,342,381 A | 8/1994 | Tidemand | 5,520,702 A | 5/1996 | Sauer et al. |
| 5,342,393 A | 8/1994 | Stack | 5,527,313 A | 6/1996 | Scott et al. |
| 5,344,424 A | 9/1994 | Roberts et al. | 5,528,833 A | 6/1996 | Sakuma |
| 5,350,391 A | 9/1994 | Iacovelli | 5,529,067 A | 6/1996 | Larsen et al. |
| 5,351,809 A | 10/1994 | Gilmore et al. | 5,531,744 A | 7/1996 | Nardella et al. |
| 5,352,222 A | 10/1994 | Rydell | 5,536,251 A | 7/1996 | Evard et al. |
| 5,354,271 A | 10/1994 | Voda | 5,540,684 A | 7/1996 | Hassler, Jr. |
| 5,356,408 A | 10/1994 | Rydell | 5,540,685 A | 7/1996 | Parins et al. |
| 5,359,993 A | 11/1994 | Slater et al. | 5,540,706 A | 7/1996 | Aust et al. |
| 5,366,477 A | 11/1994 | LeMarie, III et al. | 5,540,715 A | 7/1996 | Katsaros et al. |
| 5,367,250 A | 11/1994 | Whisenand | 5,542,945 A | 8/1996 | Fritzsch |
| 5,368,600 A | 11/1994 | Failla et al. | 5,549,604 A | 8/1996 | Sutcu et al. |
| 5,374,277 A | 12/1994 | Hassler | 5,558,671 A | 9/1996 | Yates |
| 5,376,089 A | 12/1994 | Smith | 5,558,672 A | 9/1996 | Edwards et al. |
| 5,376,094 A | 12/1994 | Kline | 5,562,619 A | 10/1996 | Mirarchi et al. |
| D354,564 S | 1/1995 | Medema | 5,562,699 A | 10/1996 | Heimberger et al. |
| 5,383,875 A | 1/1995 | Bays et al. | 5,562,720 A | 10/1996 | Stern et al. |
| 5,383,880 A | 1/1995 | Hooven | 5,564,615 A | 10/1996 | Bishop et al. |
| 5,383,897 A | 1/1995 | Wholey | 5,569,241 A | 10/1996 | Edwards |
| 5,389,098 A * | 2/1995 | Tsuruta et al. .................. 606/41 | 5,569,243 A | 10/1996 | Kortenbach et al. |
| 5,389,103 A | 2/1995 | Melzer et al. | 5,571,100 A | 11/1996 | Goble et al. |
| 5,389,104 A | 2/1995 | Hahnen et al. | 5,573,424 A | 11/1996 | Poppe |
| 5,391,166 A | 2/1995 | Eggers | 5,573,534 A | 11/1996 | Stone |
| 5,391,183 A | 2/1995 | Janzen et al. | 5,573,535 A | 11/1996 | Viklund |
| 5,395,360 A | 3/1995 | Manoukian | 5,575,799 A | 11/1996 | Bolanos et al. |
| 5,396,900 A | 3/1995 | Slater et al. | 5,575,805 A | 11/1996 | Li |
| 5,403,312 A | 4/1995 | Yates et al. | 5,578,052 A | 11/1996 | Koros et al. |
| 5,403,342 A | 4/1995 | Tovey et al. | 5,579,781 A | 12/1996 | Cooke |
| 5,405,344 A | 4/1995 | Williamson et al. | 5,582,611 A | 12/1996 | Tsuruta et al. |
| 5,409,763 A | 4/1995 | Serizawa et al. | 5,582,617 A | 12/1996 | Klieman et al. |
| D358,887 S | 5/1995 | Feinberg | 5,585,896 A | 12/1996 | Yamazaki et al. |
| 5,411,519 A | 5/1995 | Tovey et al. | 5,590,570 A | 1/1997 | LeMaire, III et al. |
| 5,411,520 A | 5/1995 | Nash et al. | 5,591,181 A | 1/1997 | Stone et al. |
| 5,413,571 A | 5/1995 | Katsaros et al. | 5,597,107 A | 1/1997 | Knodel et al. |
| 5,415,656 A | 5/1995 | Tihon et al. | 5,599,350 A | 2/1997 | Schulze et al. |
| 5,415,657 A | 5/1995 | Taymor-Luria | 5,601,224 A | 2/1997 | Bishop et al. |
| 5,417,709 A | 5/1995 | Slater | 5,601,601 A | 2/1997 | Tal et al. |
| 5,422,567 A | 6/1995 | Matsunaga | 5,601,641 A | 2/1997 | Stephens |
| 5,423,810 A | 6/1995 | Goble et al. | 5,603,711 A | 2/1997 | Parins et al. |
| 5,425,690 A | 6/1995 | Chang | 5,603,723 A | 2/1997 | Aranyi et al. |
| 5,425,739 A | 6/1995 | Jessen | 5,607,436 A | 3/1997 | Pratt et al. |
| 5,429,616 A | 7/1995 | Schaffer | 5,611,798 A | 3/1997 | Eggers |
| 5,431,672 A | 7/1995 | Cote et al. | 5,611,808 A | 3/1997 | Hossain et al. |
| 5,431,674 A | 7/1995 | Basile et al. | 5,611,813 A | 3/1997 | Lichtman |
| 5,437,292 A | 8/1995 | Kipshidze et al. | 5,618,307 A | 4/1997 | Donlon et al. |
| 5,438,302 A | 8/1995 | Goble | 5,620,415 A | 4/1997 | Lucey et al. |
| 5,439,478 A | 8/1995 | Palmer | 5,620,453 A | 4/1997 | Nallakrishnan |
| 5,441,517 A | 8/1995 | Kensey et al. | 5,620,459 A | 4/1997 | Lichtman |
| 5,443,463 A | 8/1995 | Stern et al. | 5,624,452 A | 4/1997 | Yates |
| 5,443,464 A | 8/1995 | Russell et al. | 5,626,578 A | 5/1997 | Tihon |
| 5,443,480 A | 8/1995 | Jacobs et al. | 5,626,607 A | 5/1997 | Malecki et al. |
| 5,445,638 A | 8/1995 | Rydell et al. | 5,626,609 A | 5/1997 | Zvenyatsky et al. |
| 5,445,658 A | 8/1995 | Durrfeld et al. | 5,630,833 A | 5/1997 | Katsaros et al. |
| 5,449,480 A | 9/1995 | Kuriya et al. | 5,637,110 A | 6/1997 | Pennybacker et al. |
| 5,451,224 A | 9/1995 | Goble et al. | 5,638,003 A | 6/1997 | Hall |
| 5,454,809 A | 10/1995 | Janssen | 5,639,403 A | 6/1997 | Ida et al. |
| 5,454,823 A | 10/1995 | Richardson et al. | 5,643,294 A | 7/1997 | Tovey et al. |
| 5,454,827 A | 10/1995 | Aust et al. | 5,647,869 A | 7/1997 | Goble et al. |
| 5,456,684 A | 10/1995 | Schmidt et al. | 5,647,871 A | 7/1997 | Levine et al. |
| 5,458,598 A * | 10/1995 | Feinberg et al. ................ 606/52 | 5,649,959 A | 7/1997 | Hannam et al. |
| 5,460,629 A | 10/1995 | Shlain et al. | 5,655,650 A | 8/1997 | Naitou |
| 5,461,765 A | 10/1995 | Linden et al. | 5,658,281 A | 8/1997 | Heard |
| 5,462,546 A | 10/1995 | Rydell | D384,413 S | 9/1997 | Zlock et al. |

| Patent No. | Date | Inventor |
|---|---|---|
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A * | 11/1997 | Yates et al. .................. 606/51 |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,742 A | 2/1998 | Zacharias |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,762,255 A | 6/1998 | Chrisman et al. |
| 5,762,609 A | 6/1998 | Benaron et al. |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,776,156 A | 7/1998 | Shikhman |
| 5,779,646 A | 7/1998 | Koblish et al. |
| 5,779,701 A | 7/1998 | McBrayer et al. |
| 5,779,727 A | 7/1998 | Orejola |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,797,959 A | 8/1998 | Castro et al. |
| 5,800,448 A | 9/1998 | Banko |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,083 A | 10/1998 | Shemesh et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,830,212 A | 11/1998 | Cartmell et al. |
| 5,833,690 A | 11/1998 | Yates et al. |
| 5,833,695 A | 11/1998 | Yoon |
| D402,028 S | 12/1998 | Grimm et al. |
| 5,843,080 A | 12/1998 | Fleenor et al. |
| 5,849,022 A | 12/1998 | Sakashita et al. |
| 5,851,214 A | 12/1998 | Larsen et al. |
| 5,853,412 A | 12/1998 | Mayenberger |
| 5,859,527 A | 1/1999 | Cook |
| 5,860,976 A | 1/1999 | Billings et al. |
| 5,865,361 A | 2/1999 | Milliman et al. |
| 5,876,401 A | 3/1999 | Schulze et al. |
| 5,876,410 A | 3/1999 | Petillo |
| 5,876,412 A | 3/1999 | Piraka |
| 5,882,567 A | 3/1999 | Cavallaro et al. |
| D408,018 S | 4/1999 | McNaughton |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,938,589 A | 8/1999 | Wako et al. |
| 5,941,869 A | 8/1999 | Patterson et al. |
| 5,944,718 A | 8/1999 | Dafforn et al. |
| 5,951,545 A | 9/1999 | Schilling et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| D416,089 S | 11/1999 | Barton et al. |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka |
| 6,017,354 A | 1/2000 | Culp et al. |
| 6,017,358 A | 1/2000 | Yoon et al. |
| 6,021,693 A | 2/2000 | Feng-Sing |
| 6,024,741 A | 2/2000 | Williamson, IV et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,063,103 A | 5/2000 | Hashiguchi |
| 6,066,139 A | 5/2000 | Ryan et al. |
| 6,071,283 A | 6/2000 | Nardella et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |

| Patent Number | Kind | Date | Inventor(s) |
|---|---|---|---|
| 6,090,107 | A | 7/2000 | Borgmeier et al. |
| 6,090,123 | A | 7/2000 | Culp et al. |
| 6,096,037 | A | 8/2000 | Mulier et al. |
| 6,099,537 | A | 8/2000 | Sugai et al. |
| 6,099,550 | A | 8/2000 | Yoon |
| 6,102,909 | A | 8/2000 | Chen et al. |
| 6,106,542 | A | 8/2000 | Toybin et al. |
| 6,110,171 | A | 8/2000 | Rydell |
| 6,113,596 | A | 9/2000 | Hooven et al. |
| 6,113,598 | A | 9/2000 | Baker |
| 6,117,158 | A | 9/2000 | Measamer et al. |
| 6,122,549 | A | 9/2000 | Sharkey et al. |
| 6,123,701 | A | 9/2000 | Nezhat |
| H1904 | H | 10/2000 | Yates et al. |
| 6,126,658 | A | 10/2000 | Baker |
| 6,126,665 | A | 10/2000 | Yoon |
| 6,139,563 | A | 10/2000 | Cosgrove, III et al. |
| 6,143,005 | A | 11/2000 | Yoon et al. |
| 6,152,923 | A | 11/2000 | Ryan |
| 6,152,924 | A | 11/2000 | Parins |
| 6,162,220 | A | 12/2000 | Nezhat |
| 6,171,316 | B1 | 1/2001 | Kovac et al. |
| 6,174,309 | B1 * | 1/2001 | Wrublewski et al. ............ 606/45 |
| 6,174,310 | B1 | 1/2001 | Kirwan, Jr. |
| 6,178,628 | B1 | 1/2001 | Clemens et al. |
| 6,179,834 | B1 | 1/2001 | Buysse et al. |
| 6,179,837 | B1 | 1/2001 | Hooven |
| 6,183,467 | B1 | 2/2001 | Shapeton et al. |
| 6,187,003 | B1 | 2/2001 | Buysse et al. |
| 6,190,386 | B1 | 2/2001 | Rydell |
| 6,190,400 | B1 | 2/2001 | VanDeMoer et al. |
| 6,193,718 | B1 | 2/2001 | Kortenbach et al. |
| 6,206,876 | B1 | 3/2001 | Levine et al. |
| 6,206,877 | B1 | 3/2001 | Kese et al. |
| 6,206,893 | B1 | 3/2001 | Klein et al. |
| 6,214,028 | B1 | 4/2001 | Yoon et al. |
| 6,217,602 | B1 | 4/2001 | Redmon |
| 6,217,615 | B1 | 4/2001 | Sioshansi et al. |
| 6,221,039 | B1 | 4/2001 | Durgin et al. |
| 6,223,100 | B1 | 4/2001 | Green |
| 6,224,593 | B1 | 5/2001 | Ryan et al. |
| 6,224,614 | B1 | 5/2001 | Yoon |
| 6,228,080 | B1 | 5/2001 | Gines |
| 6,228,083 | B1 | 5/2001 | Lands et al. |
| 6,248,124 | B1 | 6/2001 | Pedros et al. |
| 6,248,944 | B1 | 6/2001 | Ito |
| 6,261,307 | B1 | 7/2001 | Yoon et al. |
| 6,267,761 | B1 | 7/2001 | Ryan |
| 6,270,497 | B1 | 8/2001 | Sekino et al. |
| 6,270,508 | B1 | 8/2001 | Klieman et al. |
| 6,273,887 | B1 | 8/2001 | Yamauchi et al. |
| 6,277,117 | B1 | 8/2001 | Tetzlaff et al. |
| 6,280,458 | B1 | 8/2001 | Boche et al. |
| 6,283,961 | B1 | 9/2001 | Underwood et al. |
| D449,886 | S | 10/2001 | Tetzlaff et al. |
| 6,298,550 | B1 | 10/2001 | Kirwan |
| 6,302,424 | B1 | 10/2001 | Gisinger et al. |
| 6,309,404 | B1 | 10/2001 | Krzyzanowski |
| 6,319,262 | B1 | 11/2001 | Bates et al. |
| 6,319,451 | B1 | 11/2001 | Brune |
| 6,322,561 | B1 | 11/2001 | Eggers et al. |
| 6,322,580 | B1 | 11/2001 | Kanner |
| 6,325,795 | B1 | 12/2001 | Lindemann et al. |
| 6,329,778 | B1 | 12/2001 | Culp et al. |
| 6,334,860 | B1 | 1/2002 | Dorn |
| 6,334,861 | B1 | 1/2002 | Chandler et al. |
| D453,923 | S | 2/2002 | Olson |
| 6,345,532 | B1 | 2/2002 | Coudray et al. |
| 6,350,264 | B1 | 2/2002 | Hooven |
| D454,951 | S | 3/2002 | Bon |
| 6,352,536 | B1 | 3/2002 | Buysse et al. |
| 6,358,249 | B1 | 3/2002 | Chen et al. |
| 6,358,259 | B1 | 3/2002 | Swain et al. |
| 6,358,268 | B1 | 3/2002 | Hunt et al. |
| 6,361,534 | B1 | 3/2002 | Chen et al. |
| 6,364,879 | B1 | 4/2002 | Chen et al. |
| D457,958 | S | 5/2002 | Dycus et al. |
| D457,959 | S | 5/2002 | Tetzlaff et al. |
| 6,387,094 | B1 | 5/2002 | Eitenmuller |
| 6,391,035 | B1 | 5/2002 | Appleby et al. |
| 6,398,779 | B1 | 6/2002 | Buysse et al. |
| 6,402,747 | B1 | 6/2002 | Lindemann et al. |
| 6,409,728 | B1 | 6/2002 | Ehr et al. |
| H2037 | H | 7/2002 | Yates et al. |
| 6,419,675 | B1 | 7/2002 | Gallo, Sr. |
| 6,425,896 | B1 | 7/2002 | Baltschun et al. |
| 6,432,112 | B2 | 8/2002 | Brock et al. |
| 6,440,144 | B1 | 8/2002 | Bacher |
| 6,443,952 | B1 | 9/2002 | Mulier et al. |
| 6,443,970 | B1 | 9/2002 | Schulze et al. |
| 6,451,018 | B1 | 9/2002 | Lands et al. |
| 6,458,125 | B1 | 10/2002 | Cosmescu |
| 6,458,128 | B1 | 10/2002 | Schulze |
| 6,458,129 | B2 | 10/2002 | Scarfi |
| 6,458,130 | B1 * | 10/2002 | Frazier et al. .................... 606/51 |
| 6,461,352 | B2 | 10/2002 | Morgan et al. |
| 6,461,368 | B2 | 10/2002 | Fogarty et al. |
| 6,464,701 | B1 | 10/2002 | Hooven et al. |
| 6,464,702 | B2 | 10/2002 | Schulze et al. |
| 6,464,704 | B2 | 10/2002 | Schmaltz et al. |
| 6,471,696 | B1 | 10/2002 | Berube et al. |
| D465,281 | S | 11/2002 | Lang |
| D466,209 | S | 11/2002 | Bon |
| 6,485,489 | B2 | 11/2002 | Teirstein et al. |
| 6,488,680 | B1 | 12/2002 | Francischelli et al. |
| 6,494,888 | B1 | 12/2002 | Laufer et al. |
| 6,500,176 | B1 | 12/2002 | Truckai et al. |
| 6,506,196 | B1 | 1/2003 | Laufer |
| 6,508,815 | B1 | 1/2003 | Strul et al. |
| 6,511,480 | B1 | 1/2003 | Tetzlaff et al. |
| 6,514,215 | B1 | 2/2003 | Ouchi |
| 6,514,252 | B2 | 2/2003 | Nezhat et al. |
| 6,517,539 | B1 | 2/2003 | Smith et al. |
| 6,527,771 | B1 | 3/2003 | Weadock et al. |
| 6,533,784 | B2 | 3/2003 | Truckai et al. |
| 6,545,239 | B2 | 4/2003 | Pedersen et al. |
| 6,558,385 | B1 | 5/2003 | McClurken et al. |
| 6,562,037 | B2 | 5/2003 | Paton et al. |
| 6,569,105 | B1 | 5/2003 | Kortenbach et al. |
| 6,582,450 | B2 | 6/2003 | Ouchi |
| 6,585,735 | B1 | 7/2003 | Lands et al. |
| 6,602,252 | B2 | 8/2003 | Mollenauer |
| 6,605,790 | B2 | 8/2003 | Yoshida |
| 6,616,654 | B2 | 9/2003 | Mollenauer |
| 6,616,658 | B2 | 9/2003 | Ineson |
| 6,616,661 | B2 | 9/2003 | Wellman et al. |
| 6,620,161 | B2 | 9/2003 | Schulze et al. |
| 6,620,184 | B2 | 9/2003 | De Laforcade et al. |
| 6,626,901 | B1 | 9/2003 | Treat et al. |
| 6,629,534 | B1 | 10/2003 | St. Goar et al. |
| 6,638,287 | B2 | 10/2003 | Danitz et al. |
| 6,641,595 | B1 | 11/2003 | Moran et al. |
| 6,652,514 | B2 | 11/2003 | Ellman et al. |
| 6,652,521 | B2 | 11/2003 | Schulze |
| 6,656,173 | B1 | 12/2003 | Palermo |
| 6,656,175 | B2 | 12/2003 | Francischelli et al. |
| 6,656,177 | B2 | 12/2003 | Truckai et al. |
| 6,660,072 | B2 | 12/2003 | Chatterjee |
| 6,663,639 | B1 | 12/2003 | Laufer et al. |
| 6,663,641 | B1 | 12/2003 | Kovac et al. |
| 6,666,854 | B1 | 12/2003 | Lange |
| 6,669,696 | B2 | 12/2003 | Bacher et al. |
| 6,673,092 | B1 | 1/2004 | Bacher |
| 6,676,660 | B2 | 1/2004 | Wampler et al. |
| 6,676,676 | B2 | 1/2004 | Danitz et al. |
| 6,679,882 | B1 | 1/2004 | Kornerup |
| 6,682,527 | B2 | 1/2004 | Strul |
| 6,682,528 | B2 | 1/2004 | Frazier et al. |
| 6,685,724 | B1 | 2/2004 | Haluck |
| 6,689,131 | B2 | 2/2004 | McClurken |
| 6,692,445 | B2 | 2/2004 | Roberts et al. |
| 6,693,246 | B1 | 2/2004 | Rudolph et al. |
| 6,695,840 | B2 | 2/2004 | Schulze |
| 6,702,810 | B2 | 3/2004 | McClurken et al. |
| 6,723,092 | B2 | 4/2004 | Brown et al. |
| 6,726,068 | B2 | 4/2004 | Miller |
| 6,726,686 | B2 | 4/2004 | Buysse et al. |
| 6,726,694 | B2 | 4/2004 | Blatter et al. |

| | | | | | | |
|---|---|---|---|---|---|---|
| 6,733,498 B2 | 5/2004 | Paton et al. | 7,087,054 B2 | 8/2006 | Truckai et al. | |
| 6,733,501 B2 | 5/2004 | Levine | 7,090,673 B2 | 8/2006 | Dycus et al. | |
| 6,736,813 B2 | 5/2004 | Yamauchi et al. | 7,090,689 B2 | 8/2006 | Nagase et al. | |
| 6,743,229 B2 | 6/2004 | Buysse et al. | 7,101,371 B2 | 9/2006 | Dycus et al. | |
| 6,743,230 B2 | 6/2004 | Lutze et al. | 7,101,372 B2 | 9/2006 | Dycus et al. | |
| 6,743,239 B1 | 6/2004 | Kuehn et al. | 7,101,373 B2 | 9/2006 | Dycus et al. | |
| 6,743,240 B2 | 6/2004 | Smith et al. | 7,103,947 B2 | 9/2006 | Sartor et al. | |
| 6,755,338 B2 | 6/2004 | Hahnen et al. | 7,107,124 B2 | 9/2006 | Green | |
| 6,755,843 B2 | 6/2004 | Chung et al. | 7,112,199 B2 | 9/2006 | Cosmescu | |
| 6,756,553 B1 | 6/2004 | Yamaguchi et al. | D531,311 S | 10/2006 | Guerra et al. | |
| 6,757,977 B2 | 7/2004 | Dambal et al. | 7,115,123 B2 | 10/2006 | Knowlton et al. | |
| D493,888 S | 8/2004 | Reschke | 7,118,570 B2 | 10/2006 | Tetzlaff et al. | |
| 6,770,072 B1 | 8/2004 | Truckai et al. | 7,118,587 B2 | 10/2006 | Dycus et al. | |
| 6,773,409 B2 | 8/2004 | Truckai et al. | 7,131,860 B2 | 11/2006 | Sartor et al. | |
| 6,773,432 B1 | 8/2004 | Clayman et al. | 7,131,970 B2 | 11/2006 | Moses et al. | |
| 6,773,434 B2 | 8/2004 | Ciarrocca | 7,131,971 B2 | 11/2006 | Dycus et al. | |
| 6,773,441 B1 | 8/2004 | Laufer et al. | 7,135,020 B2 | 11/2006 | Lawes et al. | |
| 6,775,575 B2 | 8/2004 | Bommannan et al. | 7,137,980 B2 | 11/2006 | Buysse et al. | |
| 6,776,780 B2 | 8/2004 | Mulier et al. | D533,274 S | 12/2006 | Visconti et al. | |
| 6,786,905 B2 | 9/2004 | Swanson et al. | D533,942 S | 12/2006 | Kerr et al. | |
| 6,790,217 B2 | 9/2004 | Schulze et al. | 7,145,757 B2 | 12/2006 | Shea et al. | |
| 6,796,981 B2 | 9/2004 | Wham et al. | 7,147,638 B2 | 12/2006 | Chapman et al. | |
| D496,997 S | 10/2004 | Dycus et al. | 7,150,097 B2 | 12/2006 | Sremcich et al. | |
| 6,800,825 B1 | 10/2004 | Sasaki et al. | 7,150,749 B2 | 12/2006 | Dycus et al. | |
| 6,802,843 B2 | 10/2004 | Truckai et al. | 7,153,314 B2 | 12/2006 | Laufer et al. | |
| 6,808,525 B2 | 10/2004 | Latterell et al. | D535,027 S | 1/2007 | James et al. | |
| D499,181 S | 11/2004 | Dycus et al. | 7,156,842 B2 | 1/2007 | Sartor et al. | |
| 6,818,000 B2 | 11/2004 | Muller et al. | 7,156,846 B2 | 1/2007 | Dycus et al. | |
| 6,818,007 B1 | 11/2004 | Dampney et al. | 7,160,298 B2 | 1/2007 | Lawes et al. | |
| 6,821,285 B2 | 11/2004 | Laufer et al. | 7,160,299 B2 | 1/2007 | Baily | |
| 6,830,174 B2 | 12/2004 | Hillstead et al. | 7,166,106 B2 | 1/2007 | Bartel et al. | |
| 6,835,200 B2 | 12/2004 | Laufer et al. | 7,169,145 B2 | 1/2007 | Isaacson et al. | |
| 6,857,357 B2 | 2/2005 | Fujii | 7,169,146 B2 | 1/2007 | Truckai et al. | |
| D502,994 S | 3/2005 | Blake, III | 7,179,255 B2 | 2/2007 | Lettice et al. | |
| 6,860,880 B2 | 3/2005 | Treat et al. | 7,179,258 B2 | 2/2007 | Buysse et al. | |
| 6,887,240 B1 | 5/2005 | Lands et al. | D538,932 S | 3/2007 | Malik | |
| 6,889,116 B2 | 5/2005 | Jinno | 7,195,631 B2 | 3/2007 | Dumbauld | |
| 6,908,463 B2 | 6/2005 | Treat et al. | D541,418 S | 4/2007 | Schechter et al. | |
| 6,914,201 B2 | 7/2005 | Van Vooren et al. | 7,204,835 B2 | 4/2007 | Latterell et al. | |
| 6,926,716 B2 | 8/2005 | Baker et al. | 7,207,990 B2 | 4/2007 | Lands et al. | |
| 6,929,644 B2 | 8/2005 | Truckai et al. | D541,611 S | 5/2007 | Aglassinger | |
| 6,932,810 B2 | 8/2005 | Ryan | D541,938 S | 5/2007 | Kerr et al | |
| 6,932,816 B2 | 8/2005 | Phan | 7,211,084 B2 | 5/2007 | Goble et al. | |
| 6,934,134 B2 | 8/2005 | Mori et al. | 7,223,264 B2 | 5/2007 | Daniel et al. | |
| 6,936,061 B2 | 8/2005 | Sasaki | 7,223,265 B2 | 5/2007 | Keppel | |
| D509,297 S | 9/2005 | Wells | D545,432 S | 6/2007 | Watanabe | |
| 6,942,662 B2 | 9/2005 | Goble et al. | 7,232,440 B2 | 6/2007 | Dumbauld et al. | |
| 6,943,311 B2 | 9/2005 | Miyako | D547,154 S | 7/2007 | Lee et al. | |
| 6,951,559 B1 | 10/2005 | Greep | 7,238,184 B2 | 7/2007 | Megerman et al. | |
| 6,953,430 B2 | 10/2005 | Kodooka | 7,241,288 B2 | 7/2007 | Braun | |
| 6,953,461 B2 | 10/2005 | McClurken et al. | 7,241,296 B2 | 7/2007 | Buysse et al. | |
| 6,958,070 B2 | 10/2005 | Witt et al. | 7,244,257 B2 | 7/2007 | Podhajsky et al. | |
| 6,960,210 B2 | 11/2005 | Lands et al. | 7,246,734 B2 | 7/2007 | Shelton, IV | |
| 6,964,662 B2 | 11/2005 | Kidooka | 7,248,944 B2 | 7/2007 | Green | |
| 6,966,907 B2 | 11/2005 | Goble | 7,252,667 B2 * | 8/2007 | Moses et al. | 606/51 |
| 6,972,017 B2 | 12/2005 | Smith et al. | 7,255,697 B2 | 8/2007 | Dycus et al. | |
| 6,976,492 B2 | 12/2005 | Ingle et al. | 7,267,677 B2 | 9/2007 | Johnson et al. | |
| 6,977,495 B2 | 12/2005 | Donofrio | 7,270,660 B2 | 9/2007 | Ryan | |
| 6,979,786 B2 | 12/2005 | Aukland et al. | 7,270,664 B2 | 9/2007 | Johnson et al. | |
| 6,981,628 B2 | 1/2006 | Wales | 7,276,068 B2 | 10/2007 | Johnson et al. | |
| 6,987,244 B2 | 1/2006 | Bauer | 7,300,435 B2 | 11/2007 | Wham et al. | |
| 6,994,707 B2 | 2/2006 | Ellman et al. | 7,303,557 B2 | 12/2007 | Wham et al. | |
| 6,994,709 B2 | 2/2006 | Iida | 7,311,709 B2 | 12/2007 | Truckai et al. | |
| 6,997,931 B2 | 2/2006 | Sauer et al. | 7,314,471 B2 | 1/2008 | Holman | |
| 7,001,381 B2 | 2/2006 | Harano et al. | 7,318,823 B2 | 1/2008 | Sharps et al. | |
| 7,011,657 B2 | 3/2006 | Truckai et al. | 7,329,256 B2 | 2/2008 | Johnson et al. | |
| 7,033,354 B2 | 4/2006 | Keppel | 7,329,257 B2 | 2/2008 | Kanehira et al. | |
| 7,033,356 B2 | 4/2006 | Latterell et al. | D564,662 S | 3/2008 | Moses et al. | |
| 7,041,102 B2 | 5/2006 | Truckai et al. | 7,338,526 B2 | 3/2008 | Steinberg | |
| 7,044,948 B2 | 5/2006 | Keppel | 7,342,754 B2 | 3/2008 | Fitzgerald et al. | |
| 7,052,489 B2 | 5/2006 | Griego et al. | 7,344,268 B2 | 3/2008 | Jhigamian | |
| 7,052,496 B2 | 5/2006 | Yamauchi | 7,347,864 B2 | 3/2008 | Vargas | |
| 7,063,715 B2 | 6/2006 | Onuki et al. | D567,943 S | 4/2008 | Moses et al. | |
| D525,361 S | 7/2006 | Hushka | 7,354,440 B2 | 4/2008 | Truckal et al. | |
| 7,070,597 B2 | 7/2006 | Truckai et al. | 7,367,976 B2 | 5/2008 | Lawes et al. | |
| 7,083,618 B2 | 8/2006 | Couture et al. | 7,377,920 B2 | 5/2008 | Buysse et al. | |
| 7,083,619 B2 | 8/2006 | Truckai et al. | 7,384,420 B2 | 6/2008 | Dycus et al. | |
| 7,083,620 B2 | 8/2006 | Jahns et al. | 7,384,421 B2 | 6/2008 | Hushka | |
| 7,087,051 B2 | 8/2006 | Bourne et al. | 7,396,265 B2 | 7/2008 | Darley et al. | |

| | | |
|---|---|---|
| 7,396,336 B2 | 7/2008 | Orszulak et al. |
| 7,396,356 B2 | 7/2008 | Mollenauer |
| D575,395 S | 8/2008 | Hushka |
| D575,401 S | 8/2008 | Hixson et al. |
| 7,425,835 B2 | 9/2008 | Eisele |
| 7,431,721 B2 | 10/2008 | Paton et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,503,474 B2 | 3/2009 | Hillstead et al. |
| 7,510,556 B2 | 3/2009 | Nguyen et al. |
| 7,513,898 B2 | 4/2009 | Johnson et al. |
| 7,517,351 B2 | 4/2009 | Culp et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 7,582,087 B2 | 9/2009 | Tetzlaff et al. |
| 7,588,565 B2 | 9/2009 | Marchitto et al. |
| 7,594,916 B2 | 9/2009 | Weinberg |
| 7,597,693 B2 | 10/2009 | Garrison |
| 7,621,910 B2 | 11/2009 | Sugi |
| 7,628,791 B2 | 12/2009 | Garrison et al. |
| 7,628,792 B2 | 12/2009 | Guerra |
| 7,637,409 B2 | 12/2009 | Marczyk |
| 7,641,653 B2 | 1/2010 | Dalla Betta et al. |
| 7,651,493 B2 | 1/2010 | Arts et al. |
| 7,651,494 B2 | 1/2010 | McClurken et al. |
| 7,655,007 B2 | 2/2010 | Baily |
| 7,668,597 B2 | 2/2010 | Engmark et al. |
| 7,678,111 B2 | 3/2010 | Mulier et al. |
| 7,686,804 B2 | 3/2010 | Johnson et al. |
| 7,686,827 B2 | 3/2010 | Hushka |
| 7,708,735 B2 | 5/2010 | Chapman et al. |
| 7,717,115 B2 | 5/2010 | Barrett et al. |
| 7,717,904 B2 | 5/2010 | Suzuki et al. |
| 7,717,914 B2 | 5/2010 | Kimura |
| 7,717,915 B2 | 5/2010 | Miyazawa |
| 7,722,607 B2 | 5/2010 | Dumbauld et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,731,717 B2 | 6/2010 | Odom et al. |
| 7,744,615 B2 | 6/2010 | Couture |
| 7,749,217 B2 | 7/2010 | Podhajsky |
| 7,753,908 B2 | 7/2010 | Swanson |
| 7,753,909 B2 | 7/2010 | Chapman et al. |
| D621,503 S | 8/2010 | Otten et al. |
| 7,766,910 B2 | 8/2010 | Hixson et al. |
| 7,771,425 B2 | 8/2010 | Dycus et al. |
| 7,776,036 B2 | 8/2010 | Schechter et al. |
| 7,776,037 B2 | 8/2010 | Odom |
| 7,780,662 B2 | 8/2010 | Bahney |
| 7,780,663 B2 | 8/2010 | Yates et al. |
| 7,789,878 B2 | 9/2010 | Dumbauld et al. |
| 7,799,026 B2 | 9/2010 | Schechter et al. |
| 7,799,028 B2 | 9/2010 | Schechter et al. |
| 7,811,283 B2 | 10/2010 | Moses et al. |
| 7,819,872 B2 | 10/2010 | Johnson et al. |
| D627,462 S | 11/2010 | Kingsley |
| D628,289 S | 11/2010 | Romero |
| D628,290 S | 11/2010 | Romero |
| 7,828,798 B2 | 11/2010 | Buysse et al. |
| 7,832,408 B2 | 11/2010 | Shelton, IV et al. |
| 7,837,685 B2 | 11/2010 | Weinberg et al. |
| 7,842,033 B2 | 11/2010 | Isaacson et al. |
| 7,846,158 B2 | 12/2010 | Podhajsky |
| 7,846,161 B2 | 12/2010 | Dumbauld et al. |
| 7,857,812 B2 | 12/2010 | Dycus et al. |
| D630,324 S | 1/2011 | Reschke |
| 7,877,852 B2 | 2/2011 | Unger et al. |
| 7,877,853 B2 | 2/2011 | Unger et al. |
| 7,879,035 B2 | 2/2011 | Garrison et al. |
| 7,887,535 B2 | 2/2011 | Lands et al. |
| 7,887,536 B2 | 2/2011 | Johnson et al. |
| 7,896,878 B2 | 3/2011 | Johnson et al. |
| 7,901,400 B2 | 3/2011 | Wham et al. |
| 7,905,380 B2 | 3/2011 | Shelton, IV et al. |
| 7,909,820 B2 | 3/2011 | Lipson et al. |
| 7,909,823 B2 | 3/2011 | Moses et al. |
| 7,922,718 B2 | 4/2011 | Moses et al. |
| 7,922,953 B2 | 4/2011 | Guerra |
| 7,955,332 B2 | 6/2011 | Arts et al. |
| 2002/0107517 A1 | 8/2002 | Witt et al. |
| 2002/0111624 A1 | 8/2002 | Witt et al. |
| 2003/0014052 A1 | 1/2003 | Buysse et al. |
| 2003/0014053 A1 | 1/2003 | Nguyen et al. |
| 2003/0018332 A1 | 1/2003 | Schmaltz et al. |
| 2003/0069570 A1 | 4/2003 | Witzel et al. |
| 2003/0109875 A1 | 6/2003 | Tetzlaff et al. |
| 2003/0114851 A1 | 6/2003 | Truckai et al. |
| 2003/0130653 A1 | 7/2003 | Sixto, Jr. et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0115296 A1 | 6/2004 | Duffin |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0236326 A1 | 11/2004 | Schulze et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059858 A1 | 3/2005 | Frith et al. |
| 2005/0059934 A1 | 3/2005 | Wenchell et al. |
| 2005/0096645 A1 | 5/2005 | Wellman et al. |
| 2005/0149017 A1 | 7/2005 | Dycus |
| 2005/0254081 A1 | 11/2005 | Ryu et al. |
| 2005/0283148 A1 | 12/2005 | Janssen et al. |
| 2006/0052779 A1 | 3/2006 | Hammill |
| 2006/0064086 A1 | 3/2006 | Odom |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0116675 A1 | 6/2006 | McClurken et al. |
| 2006/0173452 A1 | 8/2006 | Buysse et al. |
| 2006/0190035 A1 | 8/2006 | Hushka et al. |
| 2006/0217709 A1 | 9/2006 | Couture et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0283093 A1 | 12/2006 | Petrovic et al. |
| 2006/0287641 A1 | 12/2006 | Perlin |
| 2007/0043337 A1 | 2/2007 | McAuley |
| 2007/0043353 A1 | 2/2007 | Dycus et al. |
| 2007/0062017 A1 | 3/2007 | Dycus et al. |
| 2007/0118115 A1 | 5/2007 | Artale et al. |
| 2007/0142834 A1 | 6/2007 | Dumbauld |
| 2007/0173804 A1 | 7/2007 | Wham et al. |
| 2007/0173811 A1 | 7/2007 | Couture et al. |
| 2007/0173813 A1 | 7/2007 | Odom |
| 2007/0198011 A1 | 8/2007 | Sugita |
| 2007/0213712 A1 | 9/2007 | Buysse et al. |
| 2007/0225695 A1 | 9/2007 | Mayer et al. |
| 2007/0255279 A1 | 11/2007 | Buysse et al. |
| 2007/0260238 A1 | 11/2007 | Guerra |
| 2007/0260242 A1 | 11/2007 | Dycus et al. |
| 2007/0265616 A1 | 11/2007 | Couture et al. |

| | | | | | | |
|---|---|---|---|---|---|---|
| 2008/0004616 A1 | 1/2008 | Patrick | | 2010/0069903 A1 | 3/2010 | Allen, IV et al. |
| 2008/0015575 A1 | 1/2008 | Odom et al. | | 2010/0069904 A1 | 3/2010 | Cunningham |
| 2008/0033428 A1 | 2/2008 | Artale et al. | | 2010/0069953 A1 | 3/2010 | Cunningham et al. |
| 2008/0039831 A1 | 2/2008 | Odom et al. | | 2010/0076427 A1 | 3/2010 | Heard |
| 2008/0039835 A1 | 2/2008 | Johnson et al. | | 2010/0076430 A1 | 3/2010 | Romero |
| 2008/0045947 A1 | 2/2008 | Johnson et al. | | 2010/0076431 A1 | 3/2010 | Allen, IV |
| 2008/0058802 A1 | 3/2008 | Couture et al. | | 2010/0076432 A1 | 3/2010 | Horner |
| 2008/0082100 A1 | 4/2008 | Orton et al. | | 2010/0087816 A1 | 4/2010 | Roy |
| 2008/0091189 A1 | 4/2008 | Carlton | | 2010/0087818 A1 | 4/2010 | Cunningham |
| 2008/0125767 A1 | 5/2008 | Blaha | | 2010/0094271 A1 | 4/2010 | Ward et al. |
| 2008/0125797 A1 | 5/2008 | Kelleher | | 2010/0094286 A1 | 4/2010 | Chojin |
| 2008/0195093 A1 | 8/2008 | Couture et al. | | 2010/0094287 A1 | 4/2010 | Cunningham et al. |
| 2008/0208289 A1 | 8/2008 | Darley et al. | | 2010/0100122 A1 | 4/2010 | Hinton |
| 2008/0215050 A1 | 9/2008 | Bakos | | 2010/0130971 A1 | 5/2010 | Baily |
| 2008/0234701 A1 | 9/2008 | Morales et al. | | 2010/0130977 A1 | 5/2010 | Garrison et al. |
| 2008/0243120 A1 | 10/2008 | Lawes et al. | | 2010/0145334 A1 | 6/2010 | Olson et al. |
| 2008/0249523 A1 | 10/2008 | McPherson et al. | | 2010/0145335 A1 | 6/2010 | Johnson et al. |
| 2008/0249527 A1 | 10/2008 | Couture | | 2010/0179539 A1 | 7/2010 | Nau, Jr. |
| 2008/0281311 A1 | 11/2008 | Dunning et al. | | 2010/0179543 A1 | 7/2010 | Johnson et al. |
| 2008/0294222 A1 | 11/2008 | Schechter | | 2010/0179545 A1 | 7/2010 | Twomey et al. |
| 2008/0312653 A1 | 12/2008 | Arts et al. | | 2010/0179546 A1 | 7/2010 | Cunningham |
| 2008/0319442 A1 | 12/2008 | Unger et al. | | 2010/0179547 A1 | 7/2010 | Cunningham et al. |
| 2009/0012520 A1 | 1/2009 | Hixson et al. | | 2010/0198248 A1 | 8/2010 | Vakharia |
| 2009/0015832 A1 | 1/2009 | Popovic et al. | | 2010/0204697 A1 | 8/2010 | Dumbauld et al. |
| 2009/0024126 A1 | 1/2009 | Artale et al. | | 2010/0204698 A1 | 8/2010 | Chapman et al. |
| 2009/0036881 A1 | 2/2009 | Artale et al. | | 2010/0217258 A1 | 8/2010 | Floume et al. |
| 2009/0036899 A1 | 2/2009 | Carlton et al. | | 2010/0217264 A1 | 8/2010 | Odom et al. |
| 2009/0043304 A1 | 2/2009 | Tetzlaff et al. | | 2010/0249769 A1 | 9/2010 | Nau, Jr. et al. |
| 2009/0048596 A1 | 2/2009 | Shields et al. | | 2010/0249776 A1 | 9/2010 | Kerr |
| 2009/0062794 A1 | 3/2009 | Buysse et al. | | 2010/0256635 A1 | 10/2010 | Mckenna et al. |
| 2009/0065565 A1 | 3/2009 | Cao | | 2010/0274244 A1 | 10/2010 | Heard |
| 2009/0076534 A1 | 3/2009 | Shelton, IV et al. | | 2010/0280511 A1 | 11/2010 | Rachlin et al. |
| 2009/0082766 A1 | 3/2009 | Unger et al. | | 2010/0280515 A1 | 11/2010 | Hixson et al. |
| 2009/0088738 A1 | 4/2009 | Guerra et al. | | 2010/0286691 A1 | 11/2010 | Kerr et al. |
| 2009/0088739 A1 | 4/2009 | Hushka et al. | | 2010/0307934 A1 | 12/2010 | Chowaniec et al. |
| 2009/0088740 A1 | 4/2009 | Guerra et al. | | 2010/0312235 A1 | 12/2010 | Bahney |
| 2009/0088741 A1 | 4/2009 | Hushka et al. | | 2010/0312238 A1 | 12/2010 | Schechter et al. |
| 2009/0088744 A1 | 4/2009 | Townsend | | 2010/0312242 A1 | 12/2010 | Odom |
| 2009/0088745 A1 | 4/2009 | Hushka et al. | | 2010/0331839 A1 | 12/2010 | Schechter et al. |
| 2009/0088746 A1 | 4/2009 | Hushka et al. | | 2011/0004209 A1 | 1/2011 | Lawes et al. |
| 2009/0088747 A1 | 4/2009 | Hushka et al. | | 2011/0004210 A1 | 1/2011 | Johnson et al. |
| 2009/0088748 A1 | 4/2009 | Guerra et al. | | 2011/0009864 A1 | 1/2011 | Bucciaglia et al. |
| 2009/0088749 A1 | 4/2009 | Hushka et al. | | 2011/0015632 A1 | 1/2011 | Artale |
| 2009/0088750 A1 | 4/2009 | Hushka et al. | | 2011/0018164 A1 | 1/2011 | Sartor et al. |
| 2009/0105750 A1 | 4/2009 | Price et al. | | 2011/0034918 A1 | 2/2011 | Reschke |
| 2009/0112206 A1 | 4/2009 | Dumbauld et al. | | 2011/0036183 A1 | 2/2011 | Artale et al. |
| 2009/0131934 A1 | 5/2009 | Odom et al. | | 2011/0046623 A1 | 2/2011 | Reschke |
| 2009/0149853 A1 | 6/2009 | Shields et al. | | 2011/0054467 A1 | 3/2011 | Mueller et al. |
| 2009/0149854 A1 | 6/2009 | Cunningham et al. | | 2011/0054468 A1 | 3/2011 | Dycus |
| 2009/0157071 A1 | 6/2009 | Wham et al. | | 2011/0054469 A1 | 3/2011 | Kappus et al. |
| 2009/0157072 A1 | 6/2009 | Wham et al. | | 2011/0054471 A1 | 3/2011 | Gerhardt et al. |
| 2009/0157075 A1 | 6/2009 | Wham et al. | | 2011/0054472 A1 | 3/2011 | Romero |
| 2009/0171350 A1 | 7/2009 | Dycus et al. | | 2011/0060333 A1 | 3/2011 | Mueller |
| 2009/0182327 A1 | 7/2009 | Unger | | 2011/0060334 A1 | 3/2011 | Brandt et al. |
| 2009/0182329 A1 | 7/2009 | Dycus | | 2011/0060335 A1 | 3/2011 | Harper et al. |
| 2009/0187188 A1 | 7/2009 | Guerra et al. | | 2011/0060356 A1 | 3/2011 | Reschke et al. |
| 2009/0198233 A1 | 8/2009 | Chojin | | 2011/0066174 A1 | 3/2011 | Gilbert |
| 2009/0204114 A1 | 8/2009 | Odom | | 2011/0071522 A1 | 3/2011 | Dumbauld et al. |
| 2009/0209957 A1 | 8/2009 | Schmaltz et al. | | 2011/0071523 A1 | 3/2011 | Dickhans |
| 2009/0209960 A1 | 8/2009 | Chojin | | 2011/0071525 A1 | 3/2011 | Dumbauld et al. |
| 2009/0234354 A1 | 9/2009 | Johnson et al. | | 2011/0072638 A1 | 3/2011 | Brandt et al. |
| 2009/0248021 A1 | 10/2009 | Mckenna | | 2011/0073246 A1 | 3/2011 | Brandt et al. |
| 2009/0254081 A1 | 10/2009 | Allison et al. | | 2011/0073594 A1 | 3/2011 | Bonn |
| 2009/0261804 A1 | 10/2009 | Mckenna et al. | | 2011/0077648 A1 | 3/2011 | Lee et al. |
| 2009/0292282 A9 | 11/2009 | Dycus | | 2011/0077649 A1 | 3/2011 | Kingsley |
| 2009/0318912 A1 | 12/2009 | Mayer et al. | | 2011/0082457 A1 | 4/2011 | Kerr et al. |
| 2010/0016857 A1 | 1/2010 | Mckenna et al. | | 2011/0082494 A1 | 4/2011 | Kerr et al. |
| 2010/0023009 A1 | 1/2010 | Moses et al. | | 2011/0087221 A1 | 4/2011 | Siebrecht et al. |
| 2010/0036375 A1 | 2/2010 | Regadas | | 2011/0098689 A1 | 4/2011 | Nau, Jr. et al. |
| 2010/0042100 A1 | 2/2010 | Tetzlaff et al. | | 2011/0106079 A1 | 5/2011 | Garrison et al. |
| 2010/0042140 A1 | 2/2010 | Cunningham | | 2011/0118736 A1 | 5/2011 | Harper et al. |
| 2010/0042142 A1 | 2/2010 | Cunningham | | | | |
| 2010/0042143 A1 | 2/2010 | Cunningham | | | FOREIGN PATENT DOCUMENTS | |
| 2010/0049187 A1 | 2/2010 | Carlton et al. | | CN | 201299462 | 9/2009 |
| 2010/0057081 A1 | 3/2010 | Hanna | | DE | 2415263 | 10/1975 |
| 2010/0057082 A1 | 3/2010 | Hanna | | DE | 2514501 | 10/1976 |
| 2010/0057083 A1 | 3/2010 | Hanna | | DE | 2627679 | 1/1977 |
| 2010/0057084 A1 | 3/2010 | Hanna | | DE | 3423356 | 1/1986 |
| 2010/0063500 A1 | 3/2010 | Muszala | | DE | 3612646 | 4/1987 |

| | | | | | |
|---|---|---|---|---|---|
| DE | 8712328 | 3/1988 | EP | 1785098 | 5/2007 |
| DE | 4303882 | 8/1994 | EP | 1785101 | 5/2007 |
| DE | 4403252 | 8/1995 | EP | 1810625 | 7/2007 |
| DE | 19515914 | 7/1996 | EP | 1810628 | 7/2007 |
| DE | 19506363 | 8/1996 | EP | 1842500 | 10/2007 |
| DE | 29616210 | 1/1997 | EP | 1878400 | 1/2008 |
| DE | 19608716 | 4/1997 | EP | 1929970 | 6/2008 |
| DE | 19751106 | 5/1998 | EP | 1958583 | 8/2008 |
| DE | 19751108 | 5/1999 | EP | 1990019 | 11/2008 |
| DE | 10045375 | 4/2002 | EP | 1683496 | 12/2008 |
| DE | 10 2004 026 179 | 12/2005 | EP | 1997438 | 12/2008 |
| DE | 20 2007 009165 | 10/2007 | EP | 1997439 | 12/2008 |
| DE | 20 2007 009317 | 10/2007 | EP | 1527744 | 2/2009 |
| DE | 20 2007 016233 | 3/2008 | EP | 2206474 | 7/2010 |
| DE | 19738457 | 1/2009 | GB | 623316 | 5/1949 |
| DE | 10 2008 018406 | 7/2009 | GB | 1490585 | 11/1977 |
| EP | 0364216 | 4/1990 | GB | 2214430 A | 6/1989 |
| EP | 0467501 | 1/1992 | GB | 2213416 A | 8/1989 |
| EP | 0509670 | 10/1992 | JP | 61-501068 | 9/1984 |
| EP | 0518230 | 12/1992 | JP | 6-502328 | 3/1992 |
| EP | 0541930 | 5/1993 | JP | 5-5106 | 1/1993 |
| EP | 0306123 | 8/1993 | JP | 5-40112 | 2/1993 |
| EP | 0572131 | 12/1993 | JP | 06-030945 | 2/1994 |
| EP | 0584787 | 3/1994 | JP | 6-121797 | 5/1994 |
| EP | 0589453 | 3/1994 | JP | 6-285078 | 10/1994 |
| EP | 0589555 | 3/1994 | JP | 6-511401 | 12/1994 |
| EP | 0623316 | 11/1994 | JP | 06343644 | 12/1994 |
| EP | 0624348 | 11/1994 | JP | 07265328 | 10/1995 |
| EP | 0648475 | 4/1995 | JP | 08056955 | 3/1996 |
| EP | 0650701 | 5/1995 | JP | 08252263 | 10/1996 |
| EP | 0694290 | 3/1996 | JP | 08-289895 | 11/1996 |
| EP | 0717966 | 6/1996 | JP | 8-317934 | 12/1996 |
| EP | 0754437 | 3/1997 | JP | 8317934 | 12/1996 |
| EP | 0517243 | 9/1997 | JP | 09010223 | 1/1997 |
| EP | 0853922 | 7/1998 | JP | 9-122138 | 5/1997 |
| EP | 0875209 | 11/1998 | JP | 9122138 | 5/1997 |
| EP | 0878169 | 11/1998 | JP | 10-24051 | 1/1998 |
| EP | 0887046 | 1/1999 | JP | 11-070124 | 5/1998 |
| EP | 0923907 | 6/1999 | JP | 10-155798 | 6/1998 |
| EP | 0950378 | 10/1999 | JP | 2000-102545 | 9/1998 |
| EP | 0986990 | 3/2000 | JP | 11-47150 | 2/1999 |
| EP | 1034747 | 9/2000 | JP | 11-169381 | 6/1999 |
| EP | 1034748 | 9/2000 | JP | 11-192238 | 7/1999 |
| EP | 1025807 | 10/2000 | JP | 11244298 | 9/1999 |
| EP | 1034746 | 10/2000 | JP | 2000-342599 | 12/2000 |
| EP | 1050278 | 11/2000 | JP | 2000-350732 | 12/2000 |
| EP | 1053719 | 11/2000 | JP | 2001-008944 | 1/2001 |
| EP | 1053720 | 11/2000 | JP | 2001-029356 | 2/2001 |
| EP | 1055399 | 11/2000 | JP | 2001-128990 | 5/2001 |
| EP | 1055400 | 11/2000 | JP | 2001-190564 | 7/2001 |
| EP | 1080694 | 3/2001 | JP | 2002-136535 | 5/2002 |
| EP | 1082944 | 3/2001 | JP | 2003-175052 | 6/2003 |
| EP | 1159926 | 12/2001 | JP | 2004-517668 | 6/2004 |
| EP | 1177771 | 2/2002 | JP | 2004-528869 | 9/2004 |
| EP | 0 722 696 | 12/2002 | SU | 401367 | 11/1974 |
| EP | 1278007 | 1/2003 | WO | WO 89/00757 | 1/1989 |
| EP | 1301135 | 4/2003 | WO | WO 92/04873 | 4/1992 |
| EP | 1330991 | 7/2003 | WO | WO 92/06642 - | 4/1992 |
| EP | 1486177 | 6/2004 | WO | WO 93/19681 | 10/1993 |
| EP | 1472984 | 11/2004 | WO | WO 93/21845 | 11/1993 |
| EP | 0774232 | 1/2005 | WO | WO 94/00059 | 1/1994 |
| EP | 1527747 | 5/2005 | WO | WO 94/08524 | 4/1994 |
| EP | 1530952 | 5/2005 | WO | WO 94/20025 | 9/1994 |
| EP | 1532932 | 5/2005 | WO | WO 95/02369 | 1/1995 |
| EP | 1535581 | 6/2005 | WO | WO 95/07662 | 3/1995 |
| EP | 1609430 | 12/2005 | WO | WO 95/15124 | 6/1995 |
| EP | 1201192 | 2/2006 | WO | WO 95/20360 | 8/1995 |
| EP | 1632192 | 3/2006 | WO | WO 96/05776 | 2/1996 |
| EP | 1186274 | 4/2006 | WO | WO 96/11635 | 4/1996 |
| EP | 1642543 | 4/2006 | WO | WO 96/022056 | 7/1996 |
| EP | 1645238 | 4/2006 | WO | WO 96/13218 | 9/1996 |
| EP | 1645240 | 4/2006 | WO | WO 97/00646 | 1/1997 |
| EP | 1649821 | 4/2006 | WO | WO 97/00647 | 1/1997 |
| EP | 1707143 | 10/2006 | WO | WO 97/10764 | 3/1997 |
| EP | 1545360 | 3/2007 | WO | WO 97/18768 | 5/1997 |
| EP | 1767163 | 3/2007 | WO | WO 97/24073 | 7/1997 |
| EP | 1769765 | 4/2007 | WO | WO 97/24993 | 7/1997 |
| EP | 1769766 | 4/2007 | WO | WO 98/14124 | 4/1998 |
| EP | 1785097 | 5/2007 | WO | WO 98/27880 | 7/1998 |

| | | |
|---|---|---|
| WO | WO 98/31290 | 7/1998 |
| WO | WO 98/43264 | 10/1998 |
| WO | WO 99/03407 | 1/1999 |
| WO | WO 99/03408 | 1/1999 |
| WO | WO 99/03409 | 1/1999 |
| WO | WO 99/03414 | 1/1999 |
| WO | WO 99/12488 | 3/1999 |
| WO | WO 99/23933 | 5/1999 |
| WO | WO 99/025261 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/33753 | 6/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/01847 | 1/2001 |
| WO | WO 01/15614 | 3/2001 |
| WO | WO 01/17448 | 3/2001 |
| WO | WO 01/54604 | 8/2001 |
| WO | WO 02/07627 | 1/2002 |
| WO | WO 02/058544 | 8/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/096880 | 11/2003 |
| WO | WO 03/101311 | 12/2003 |
| WO | WO 2004/028585 | 4/2004 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/009255 | 2/2005 |
| WO | WO 2005/011049 | 2/2005 |
| WO | WO 2005/030071 | 4/2005 |
| WO | WO 2005/048809 | 6/2005 |
| WO | WO 2005/050151 | 6/2005 |
| WO | WO 2005/110264 | 11/2005 |
| WO | WO 2008/008457 | 1/2008 |
| WO | WO 2008/040483 | 4/2008 |
| WO | WO 2008/045348 | 4/2008 |
| WO | WO 2008/045350 | 4/2008 |
| WO | WO 2008/0112147 | 9/2008 |
| WO | WO 2009/0005850 | 1/2009 |
| WO | WO 2009/0039179 | 3/2009 |
| WO | WO 2009/0039510 | 3/2009 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.
U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/048,679, filed Mar. 15, 2011, Paul Guerra.
U.S. Appl. No. 13/075,847, filed Mar. 30, 2011, Gary M. Couture.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.

Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Intl Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Intl Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181969.6 dated Feb. 4, 2011.
Int'l Search Report EP 10 191320.0 dated Feb. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Japanese Office Action dated Mar. 3, 2011.
Notice of Final Rejection regarding Japanese Patent Application 2005-181315.
Official Action—Decision for Final Rejection issued in corresponding Japanese Application No. 2004-366797 dated May 16, 2011.
Inquiry mailed Mar. 8, 2012 in corresponding Japanese Application No. 2005-181315 (English translation).
Notification of Reasons for Rejection mailed May 14, 2012 in corresponding Japanese Application No. 2010-246421 (English translation).

* cited by examiner

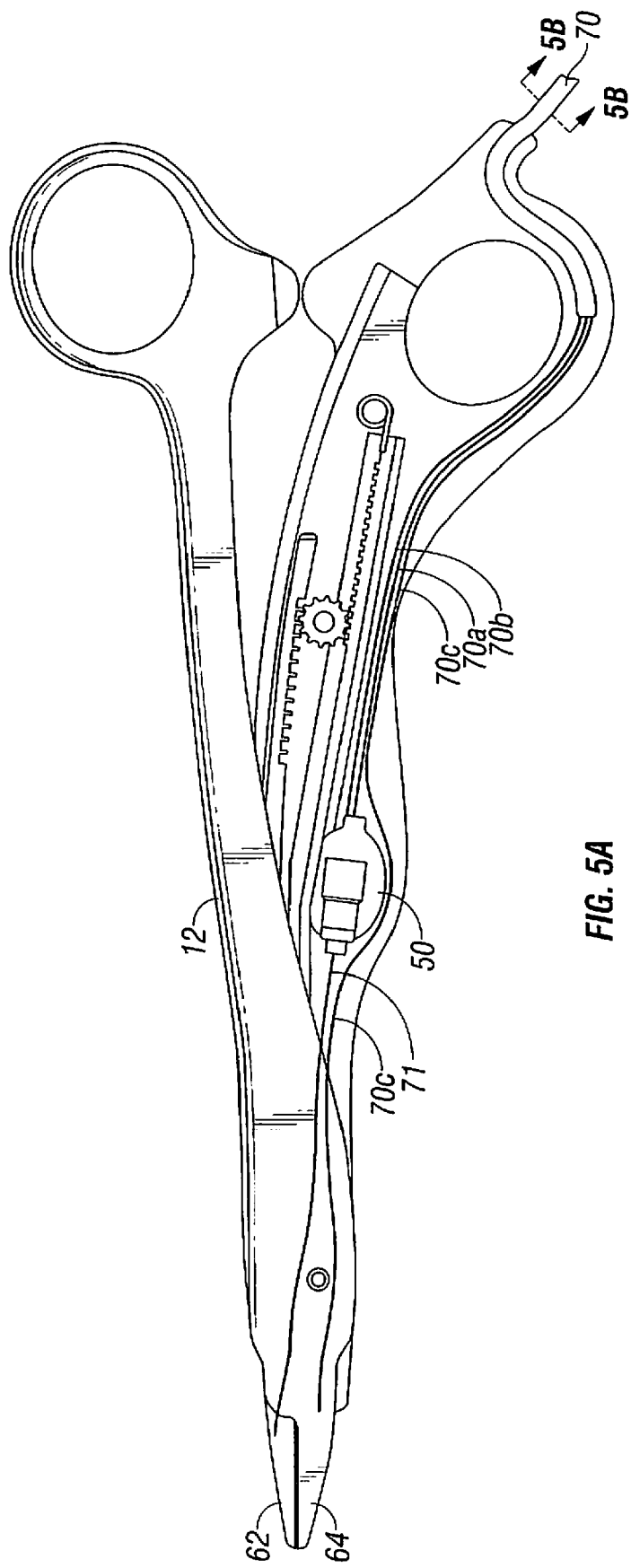
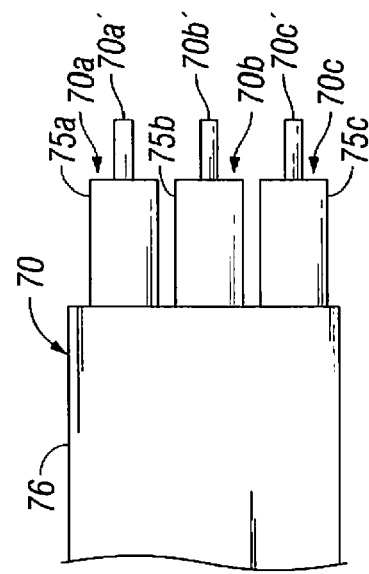
FIG. 5C
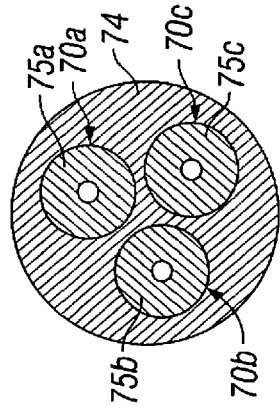
FIG. 5B
FIG. 5A

OPEN VESSEL SEALING INSTRUMENT WITH CUTTING MECHANISM

CROSS-REFERENCE TO RELATED APPLICATIONS

This application is a continuation of U.S. application Ser. No. 11/546,838 filed Oct. 12, 2006, now U.S. Pat. No. 7,922,718, which is a continuation of and claims the benefit of priority to U.S. application Ser. No. 10/991,157 filed Nov. 17, 2004, now U.S. Pat. No. 7,131,970, which claims the benefit of priority to U.S. Provisional Application Serial No. 60/523,387 filed on Nov. 19, 2003, the entire contents of each of which is incorporated herein by reference.

BACKGROUND

The present disclosure relates to forceps used for open surgical procedures. More particularly, the present disclosure relates to an open forceps which applies a combination of mechanical clamping pressure and electrosurgical energy to seal tissue and a knife which is selectively activateable to sever tissue.

TECHNICAL FIELD

A forceps is a plier-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize both mechanical clamping action and electrical energy to effect hemostasis by heating tissue and blood vessels to coagulate and/or cauterize tissue.

Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Vessel sealing or tissue sealing is a recently-developed technology which utilizes a unique combination of radio frequency energy, pressure and gap control to effectively seal or fuse tissue between two opposing jaw members or sealing plates. Vessel or tissue sealing is more than "cauterization" which is defined as the use of heat to destroy tissue (also called "diathermy" or "electrodiathermy") and vessel sealing is more than "coagulation" which is defined as a process of desiccating tissue wherein the tissue cells are ruptured and dried. "Vessel sealing" is defined as the process of liquefying the collagen, elastin and ground substances in the tissue so that it reforms into a fused mass with significantly-reduced demarcation between the opposing tissue structures.

In order to effectively "seal" tissue or vessels, two predominant mechanical parameters must be accurately controlled: 1) the pressure applied to the vessel or tissue; and 2) the gap distance between the conductive tissue contacting surfaces (electrodes). As can be appreciated, both of these parameters are affected by the thickness of the tissue being sealed. Accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal. It has been determined that a good seal for certain tissues is optimum between 0.001 inches and 0.006 inches.

With respect to smaller vessels or tissue, the pressure applied becomes less relevant and the gap distance between the electrically conductive surfaces becomes more significant for effective sealing. In other words, the chances of the two electrically conductive surfaces touching during activation increases as the tissue thickness and the vessels become smaller.

Commonly owned, U.S. Pat. No. 6,511,480, PCT Patent Application Nos. PCT/US01/11420 and PCT/US01/11218, U.S. patent applications Ser. Nos. 10/116,824, 10/284,562 and 10/299,650 all describe various open surgical forceps which seal tissue and vessels. All of these references are hereby incorporated by reference herein. In addition, several journal articles have disclosed methods for sealing small blood vessels using electrosurgery. An article entitled *Studies on Coagulation and the Development of an Automatic Computerized Bipolar Coagulator*, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp. 187-190, describes a method for terminating electrosurgical power to the vessel so that charring of the vessel walls can be avoided.

Typically and particularly with respect to open electrosurgical procedures, once a vessel is sealed, the surgeon has to remove the sealing instrument from the operative site, substitute a new instrument and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue sealing line.

Many endoscopic vessel sealing instruments have been designed which incorporate a knife or blade member which effectively severs the tissue after forming a tissue seal. For example, commonly-owned U.S. application Ser. Nos. 10/116,944 and 10/179,863 describe one such endoscopic instrument which effectively seals and cuts tissue along the tissue seal. Other instruments include blade members or shearing members which simply cut tissue in a mechanical and/or electromechanical manner and are relatively ineffective for vessel sealing purposes.

There exists a need to develop an open electrosurgical forceps which is simple, reliable and inexpensive to manufacture and which effectively seals tissue and vessels and which allows a surgeon to utilize the same instrument to effectively sever the tissue along the newly formed tissue seal.

SUMMARY

The present disclosure relates to an open electrosurgical forceps for sealing tissue and includes a pair of first and second shaft members each having a jaw member disposed at a distal end thereof. The jaw members are movable from a first position in spaced relation relative to one another to at least one subsequent position wherein the jaw members cooperate to grasp tissue therebetween. Each of the jaw members includes an electrically conductive sealing plate or sealing surface on an inner facing surface which communicates electrosurgical energy through tissue held therebetween. Preferably, one of the jaw members includes a cutting slot defined along a longitudinal length thereof which is dimensioned to reciprocate a cutting instrument therealong to sever tissue held between the jaw members. An actuator is included for selectively advancing the cutting instrument from a first position wherein the cutting instrument is disposed proximal to tissue held between the jaw members to at least one subsequent position wherein the cutting instrument is disposed distal to tissue held between the jaw members.

In one embodiment, the actuator includes a trigger assembly which cooperates with a pulley and cable system to advance the cutting instrument from the first to second positions through tissue held therebetween. The trigger assembly of the actuator may be moved proximally, distally or laterally to distally advance the cutting instrument through the cutting slot.

Preferably, the forceps includes a safety mechanism or lockout to prevent reciprocation of the cutting instrument when the jaws are disposed in the first position. The lock out may form part of the trigger assembly and/or part of one or both of the jaw assemblies.

In one embodiment, each of the shafts includes a handle and at least one of the handle defines a track therethrough for reciprocating a cable of the pulley and cable system. The cable is mechanically engaged with the cutting instrument such that movement of the cable imparts movement of the cutting instrument between the first and subsequent positions. Preferably, the cable is manufactured from a plastic or braided flexible material and may include one or more stiffeners to prevent the cable from buckling within the track.

In another embodiment, the forceps includes one or more springs which automatically bias the cutting instrument in the first position such that after the cutting instrument severs the tissue held between the jaw members, the cutting instrument automatically returns to the first position. Preferably, the trigger assembly includes at least one spring for automatically returning the cutting instrument back to the first position.

In another embodiment, the actuator includes a trigger assembly which cooperates with a rack and pinion system to advance the cutting instrument from the first to second positions through tissue held therebetween. Preferably, the rack and pinion system is engaged with one of the first and second shaft members. The trigger assembly of the actuator may be moved proximally, distally or laterally to distally advance the cutting instrument through the cutting slot.

The present invention also relates to an open electrosurgical forceps for sealing tissue which includes a pair of first and second shaft members each having a jaw member disposed at a distal end thereof. The jaw members are movable from a first position in spaced relation relative to one another to a subsequent position wherein the jaw members cooperate to grasp tissue therebetween. One of the shaft members includes a flange that mechanically interfaces with a corresponding opening defined within the other of the shaft members. Each of the jaw members includes an electrically conductive sealing plate for communicating electrosurgical energy through tissue held therebetween. At least one of the jaw members includes a cutting slot defined along a length thereof that is dimensioned to reciprocate a cutting instrument therealong. An actuator is included which selectively reciprocates the cutting instrument to cut tissue disposed between the jaw members. A lockout is also included which has a spring biased within the opening defined in the corresponding shaft member to prevent reciprocation of the cutting instrument when the jaw members are disposed in the first position. The spring is disengaged by the flange when the jaw members are moved to the second position.

In one embodiment, the flange includes an aperture defined therein which allows reciprocation of a safety bar of the cutting instrument therethrough when the jaw members are moved to the second position. The lockout is preferably disposed within a proximal end of the forceps and the spring is configured to disengage into a chamber recessed within the corresponding shaft member.

In another embodiment according to the present disclosure, a forceps is provided which includes a lockout mechanism having a notch defined within a portion of the cutting instrument. The notch is configured to mechanically engage a corresponding detent on the pivot to prevent reciprocation of the cutting instrument when the jaw members are disposed in the first position. The notch automatically disengages from the detent when the jaw members are moved to the second position to permit selective reciprocation of the cutting instrument. The notch may be defined within a drive rod of the cutting instrument.

Still another embodiment of the present disclosure relates to an open electrosurgical forceps for sealing tissue having a pair of first and second shaft members each having a jaw member disposed at a distal end thereof. The jaw members are movable about a pivot from a first position in spaced relation relative to one another to a subsequent position wherein the jaw members cooperate to grasp tissue therebetween. Each of the jaw members is curved relative to a longitudinal axis defined through the shaft members and each jaw member includes a correspondingly curved electrically conductive sealing plate which communicates electrosurgical energy through tissue held therebetween. One (or both) of the jaw members includes a substantially curved cutting slot defined along a length thereof which is dimensioned to reciprocate a substantially flexible cutting instrument therealong via an actuator. A lockout operatively couples to the cutting instrument and is configured to prevent reciprocation of the cutting instrument when the jaw members are disposed in the first position.

In yet still another embodiment, one (or both) of the jaw members may include a substantially straight cutting slot defined along a length thereof which is dimensioned to reciprocate a cutting instrument therealong via an actuator.

BRIEF DESCRIPTION OF THE DRAWINGS

Various embodiments of the subject instrument are described herein with reference to the drawings wherein:

FIG. 5A is an internal, side view of a forceps according to the present disclosure showing an electrosurgical cable and the various internal electrical connections therein;

FIG. 5B is a cross section of the electrosurgical cable taken along line 5B-5B of FIG. 5A;

FIG. 5C is a side view of the electrosurgical cable with part of the outer insulative sheathing removed;

DETAILED DESCRIPTION

Figure 1A:
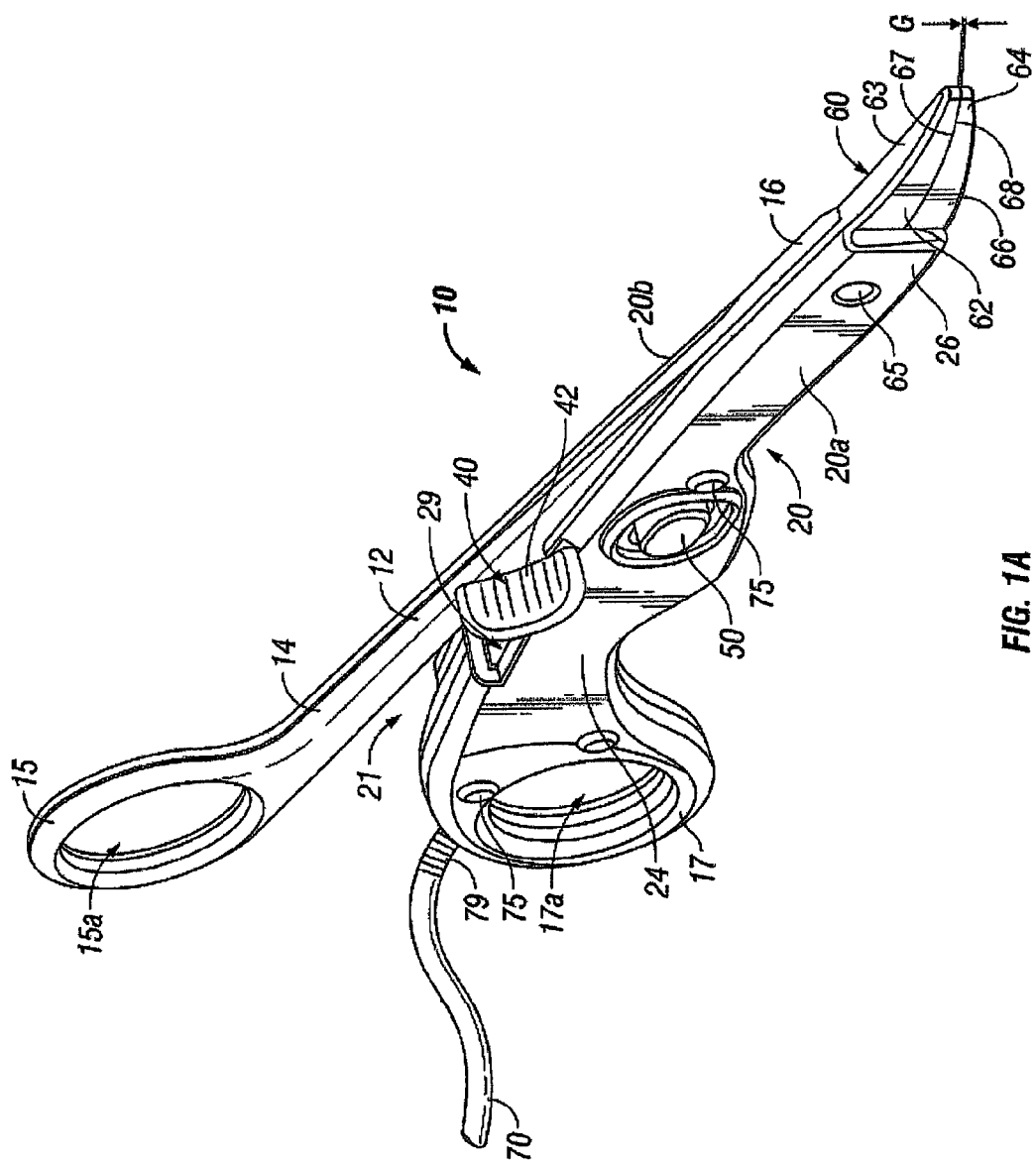
FIG. 1A is a left, perspective view of an open forceps according to the present disclosure.

Referring now to FIGS. 1A-1E, a forceps 10 for use with open surgical procedures includes elongated shaft portions 12 and 20 each having a proximal end 14 and 24, respectively, and a distal end 16 and 26, respectively. In the drawings and in the descriptions which follow, the term "proximal", as is traditional, will refer to the end of the forceps 10 which is closer to the user, while the term "distal" will refer to the end which is further from the user.

The forceps 10 includes an end effector assembly 60 which attaches to the distal ends 16 and 26 of shafts 12 and 20, respectively. As explained in more detail below, the end effector assembly 60 includes pair of opposing jaw members 62 and 64 which are pivotably connected about a pivot pin 65 and which are movable relative to one another to grasp tissue.

Preferably, each shaft 12 and 20 includes a handle 15 and 17, disposed at the proximal end 14 and 24 thereof which each define a finger hole 15a and 17a, respectively, therethrough for receiving a finger of the user. As can be appreciated, finger holes 15a and 17a facilitate movement of the shafts 12 and 20 relative to one another which, in turn, pivot the jaw members 62 and 64 from an open position wherein the jaw members 62 and 64 are disposed in spaced relation relative to one another to a clamping or closed position wherein the jaw members 62 and 64 cooperate to grasp tissue therebetween.

As best seen in FIG. 1A, shaft 20 is bifurcated to define an elongated channel 21 therealong which is dimensioned to receive shaft 12 therein. More particularly, shaft 20 is made from two halves 20a and 20b which are matingly engaged during assembly to form shaft 20 and to define the elongated channel 21. It is envisioned that the two halves 20a and 20b may be sonic-welded together at a plurality of different weld points 75 or the housing halves may be mechanically engaged in any other known fashion, snap-fit, glued, screwed, etc. Upon assembly, shaft 12 is positioned within shaft 20 and secured about pivot 65 which allows the two shafts 12 and 20 to pivot with respect to one another. When the user moves the shaft 12 relative to shaft 20 to close the jaw members 62 and 64, shaft 12 is received within the elongated channel 21 of shaft 20. It is envisioned that configuring the two shafts 12 and 20 in the fashion facilitates gripping and reduces the overall size of the forceps 10 which is especially advantageous during surgeries in small cavities.

As best illustrated in FIG. 1A, one of the shafts, e.g., 20, includes a proximal shaft connector 79 which is designed to connect the forceps 10 to a source of electrosurgical energy such as an electrosurgical generator (not shown). The proximal shaft connector 79 electromechanically engages an electrosurgical cable 70 such that the user may selectively apply electrosurgical energy as needed. Alternatively, the cable 70 may be fed directly into shaft 20 as best seen in FIG. 5A.

As explained in more detail below, the distal end of the cable 70 connects to a handswitch 50 to permit the user to selectively apply electrosurgical energy as need to seal tissue grasped between jaw members 62 and 64. More particularly, the interior of cable 70 houses leads 70a, 70b and 70c which upon activation of the handswitch 50 conduct the different electrical potentials from the electrosurgical generator to the jaw members 62 and 64. As can be appreciated, positioning the switch 50 on the forceps 10 gives the user more visual and tactile control over the application of electrosurgical energy. These aspects are explained below with respect to FIGS. 5A-5C and the discussion of the handswitch 50 and the electrical connections associated therewith.

Figure 1B:
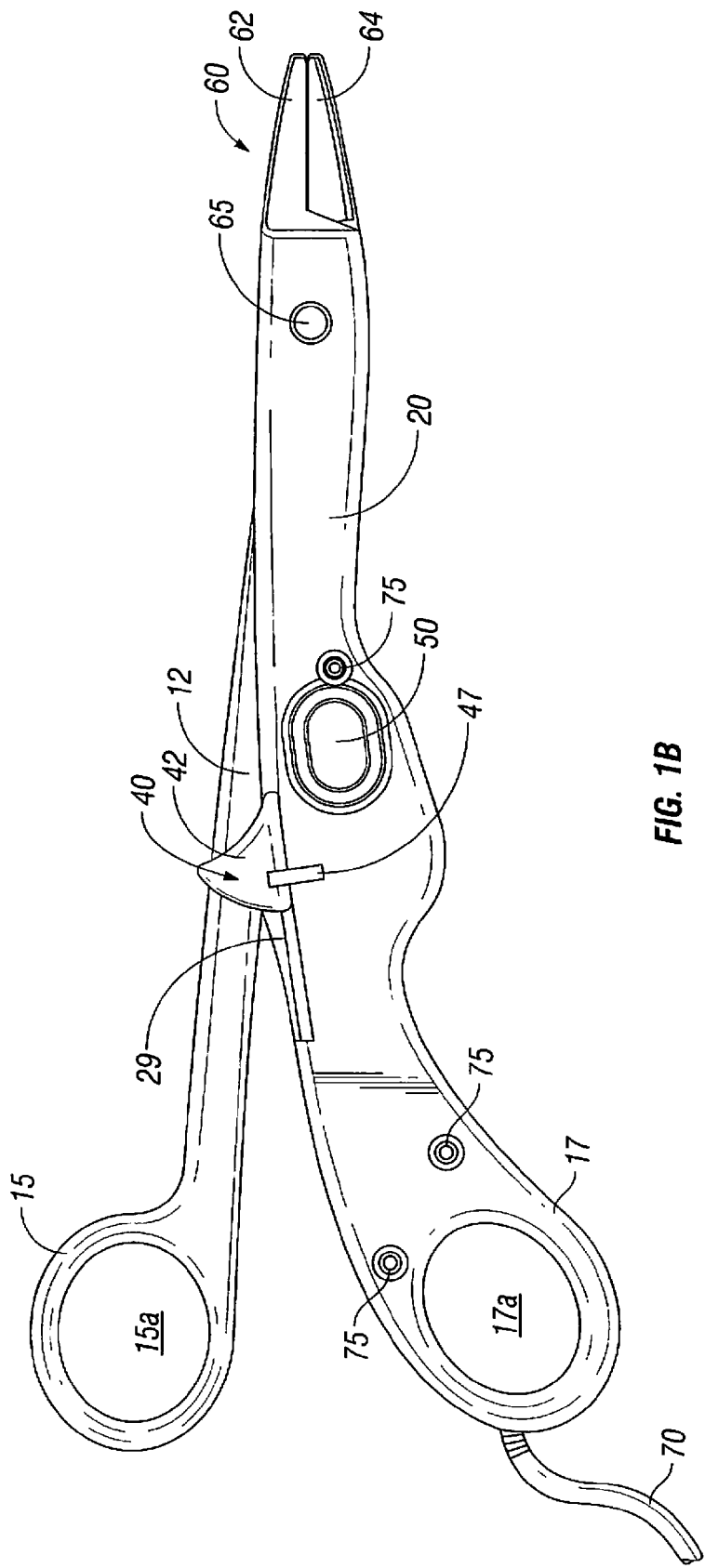
FIG. 1B is a left, side view of the forceps of FIG. 1A.

As best seen in FIGS. 1A and 1B, the two opposing jaw members 62 and 64 of the end effector assembly 60 are pivotable about pin 65 from the open position to the closed position for grasping tissue therebetween. Jaw members 62 and 64 are generally symmetrical and include similar component features which cooperate to permit facile rotation about pivot pin 65 to effect the grasping and sealing of tissue. As a result and unless otherwise noted, jaw member 62 and the operative features associated therewith are initially described herein in detail and the similar component features with respect to jaw member 64 will be briefly summarized thereafter. Moreover, many of the features of the jaw members 62 and 64 are described in detail in commonly-owned U.S. patent application Ser. Nos. 10/284,562, 10/116,824, 09/425,696, 09/178,027 and PCT Application Serial No. PCT/US01/11420 the contents of which are all hereby incorporated by reference in their entirety herein.

Jaw member 62 includes an insulated outer housing 63 which is dimensioned to mechanically engage an electrically conductive sealing surface 67. The outer insulative housing 63 extends along the entire length of jaw member 62 to reduce alternate or stray current paths during sealing and/or incidental burning of tissue. The electrically conductive surface 67 conducts electrosurgical energy of a first potential to the tissue upon activation of the handswitch 50. Insulated outer housing 63 is dimensioned to securely engage the electrically conductive sealing surface 67. It is envisioned that this may be accomplished by stamping, by overmolding, by overmolding a stamped electrically conductive sealing plate and/or by overmolding a metal injection molded seal plate. Other methods of affixing the seal surface 67 to the outer housing 63 are described in detail in one or more of the above-identified references.

It is also envisioned that the electrically conductive sealing surface 67 may include a pinch trim (not shown) which facilitates secure engagement of the electrically conductive surface 67 to the insulated outer housing 63 and also simplifies the overall manufacturing process. It is also contemplated that the electrically conductive sealing surface 67 may include an outer peripheral edge which has a radius and the insulated outer housing 63 meets the electrically conductive sealing surface 67 along an adjoining edge which is generally tangential to the radius and/or meets along the radius. Preferably, at the interface, the electrically conductive surface 67 is raised relative to the insulated outer housing 63. These and other envisioned embodiments are discussed in commonly-owned, co-pending PCT Application Serial No. PCT/US01/11412 and commonly owned, co-pending PCT Application Serial No. PCT/US01/11411, the contents of both of these applications being incorporated by reference herein in their entirety.

Preferably, the insulated outer housing 63 and the electrically conductive sealing surface 67 are dimensioned to limit and/or reduce many of the known undesirable effects related to tissue sealing, e.g., flashover, thermal spread and stray current dissipation. All of the aforementioned and cross referenced manufacturing techniques produce an electrode having an electrically conductive surface 67 which is substantially surrounded by an insulated outer housing 63.

Likewise, jaw member 64 includes similar elements which include: an outer housing 66 which engages an electrically conductive sealing surface 68. The electrically conducive sealing surface 68 conducts electrosurgical energy of a second potential to the tissue upon activation of the handswitch 50.

It is envisioned that one of the jaw members, e.g., 62, includes at least one stop member (not shown) disposed on the inner facing surface of the electrically conductive sealing surface 67 (and/or 68). Alternatively or in addition, the stop member may be positioned adjacent to the electrically conductive sealing surfaces 67, 68 or proximate the pivot pin 65. The stop member(s) is preferably designed to facilitate gripping and manipulation of tissue and to define a gap "G" (FIG. 1A) between opposing jaw members 62 and 64 during sealing. Preferably the separation distance during sealing or the gap distance "G" is within the range of about 0.001 inches (~0.03 millimeters) to about 0.006 inches (~0.016 millimeters).

A detailed discussion of these and other envisioned stop members as well as various manufacturing and assembling processes for attaching, disposing, depositing and/or affixing the stop members to the electrically conductive sealing surfaces 67, 68 are described in commonly-assigned, co-pending PCT Application Serial No. PCT/US01/11222 which is hereby incorporated by reference in its entirety herein.

As mentioned above, two mechanical factors play an important role in determining the resulting thickness of the sealed tissue and effectiveness of the seal, i.e., the pressure applied between opposing jaw members 62 and 64 and the gap "G" between the opposing jaw members 62 and 64 (or opposing seal surface 67 and 68 during activation). It is known that the thickness of the resulting tissue seal cannot be adequately controlled by force alone. In other words, too much force and the two jaw members 62 and 64 would touch and possibly short resulting in little energy traveling through the tissue thus resulting in a bad seal. Too little force and the seal would be too thick. Applying the correct force is also important for other reasons: to oppose the walls of the vessel; to reduce the tissue impedance to a low enough value that allows enough current through the tissue; and to overcome the forces of expansion during tissue heating in addition to contributing towards creating the required end tissue thickness which is an indication of a good seal.

Preferably, the seal surfaces 67 and 68 are relatively flat to avoid current concentrations at sharp edges and to avoid arcing between high points. In addition and due to the reaction force of the tissue when engaged, jaw members 62 and 64 are preferably manufactured to resist bending, i.e., tapered along their length which provides a constant pressure for a constant tissue thickness at parallel and the thicker proximal portion of the jaw members 62 and 64 will resist bending due to the reaction force of the tissue.

Figure 1C:
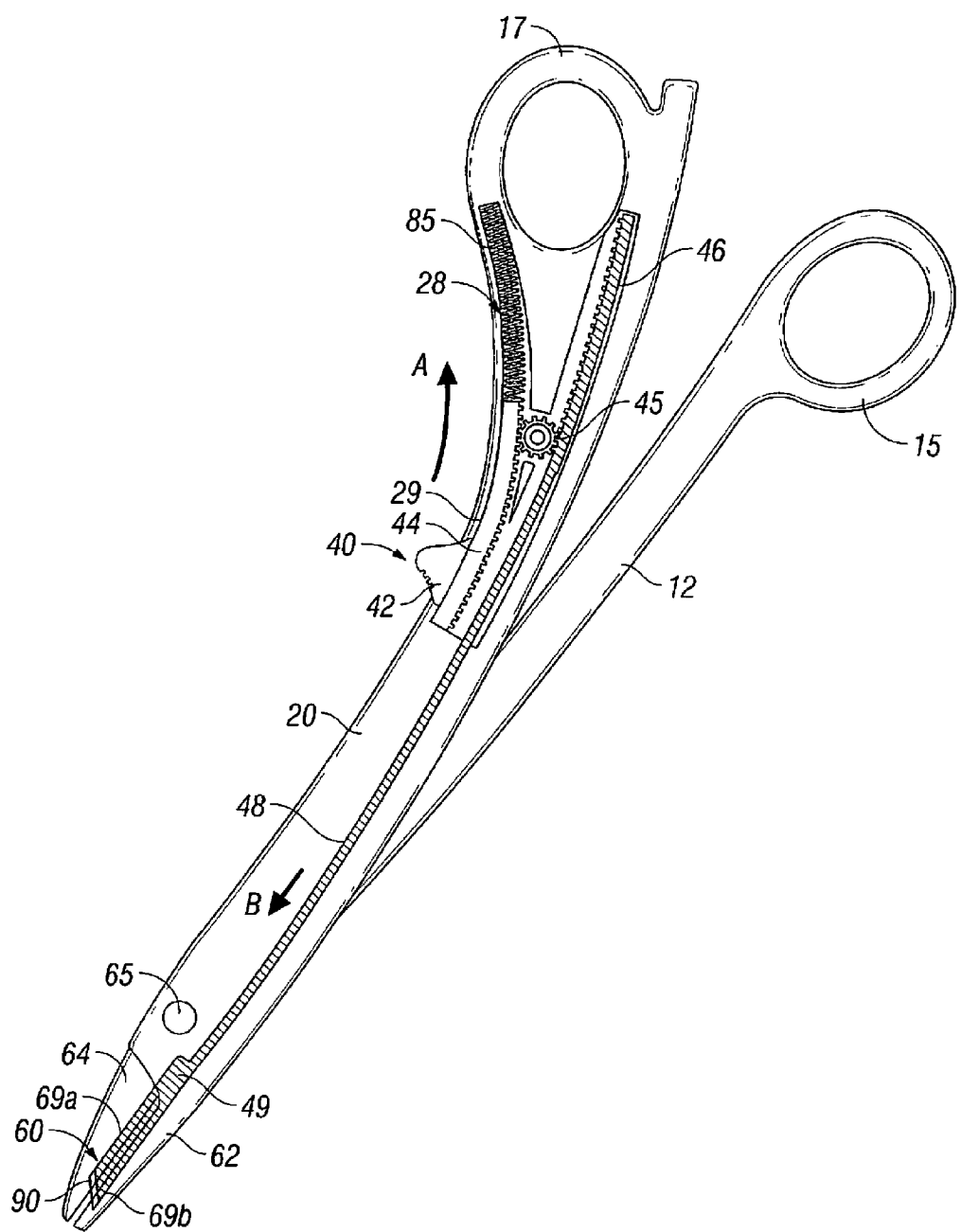
FIG. 1C is an internal view of the forceps of FIG. 1A showing a rack and pinion actuating mechanism for advancing a cutting knife.
Figure 1D:
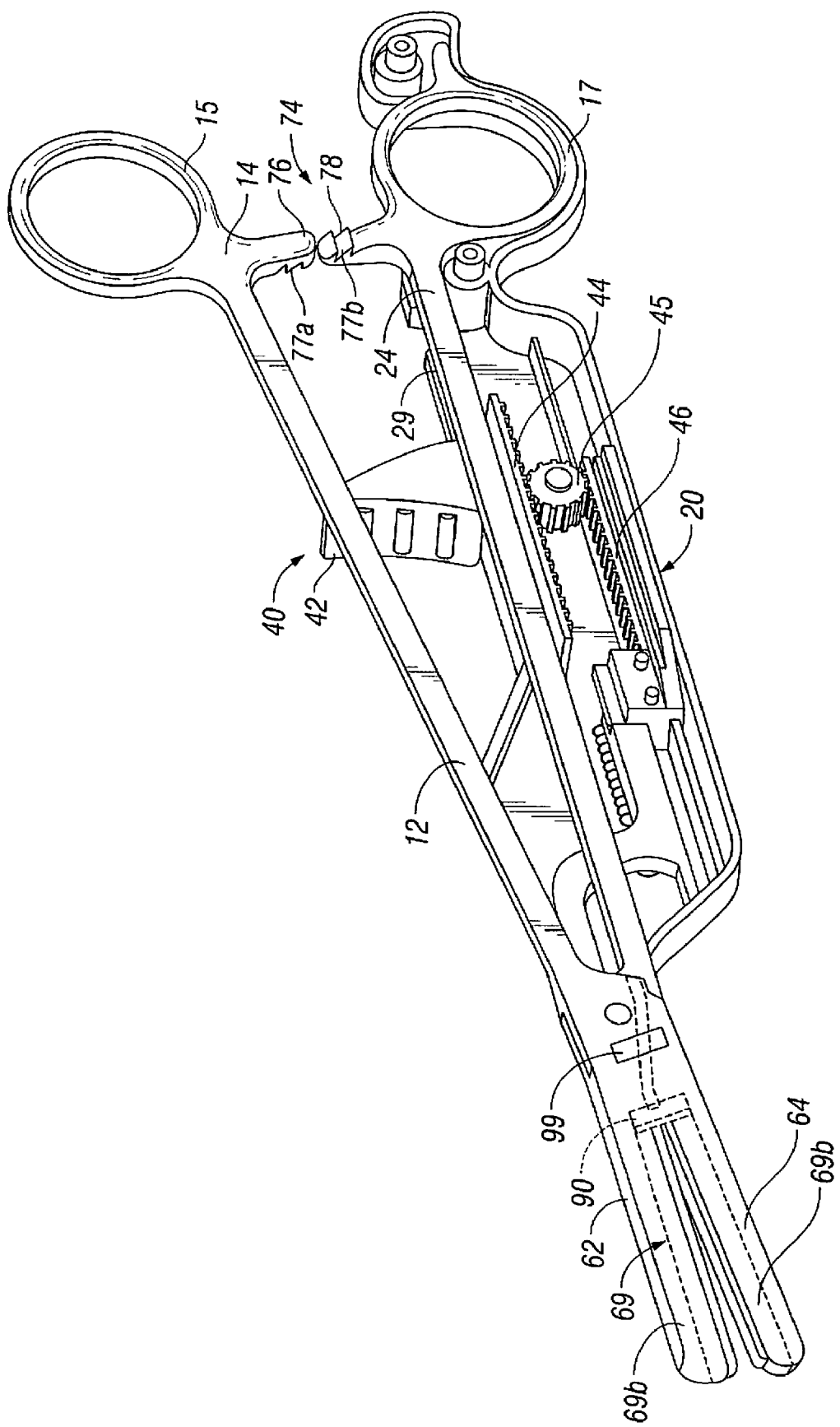
FIG. 1D is an internal, perspective view of an alternate embodiment of the open forceps according to the present disclosure having a rack and pinion actuating mechanism for advancing the cutting knife.
Figure 1E:
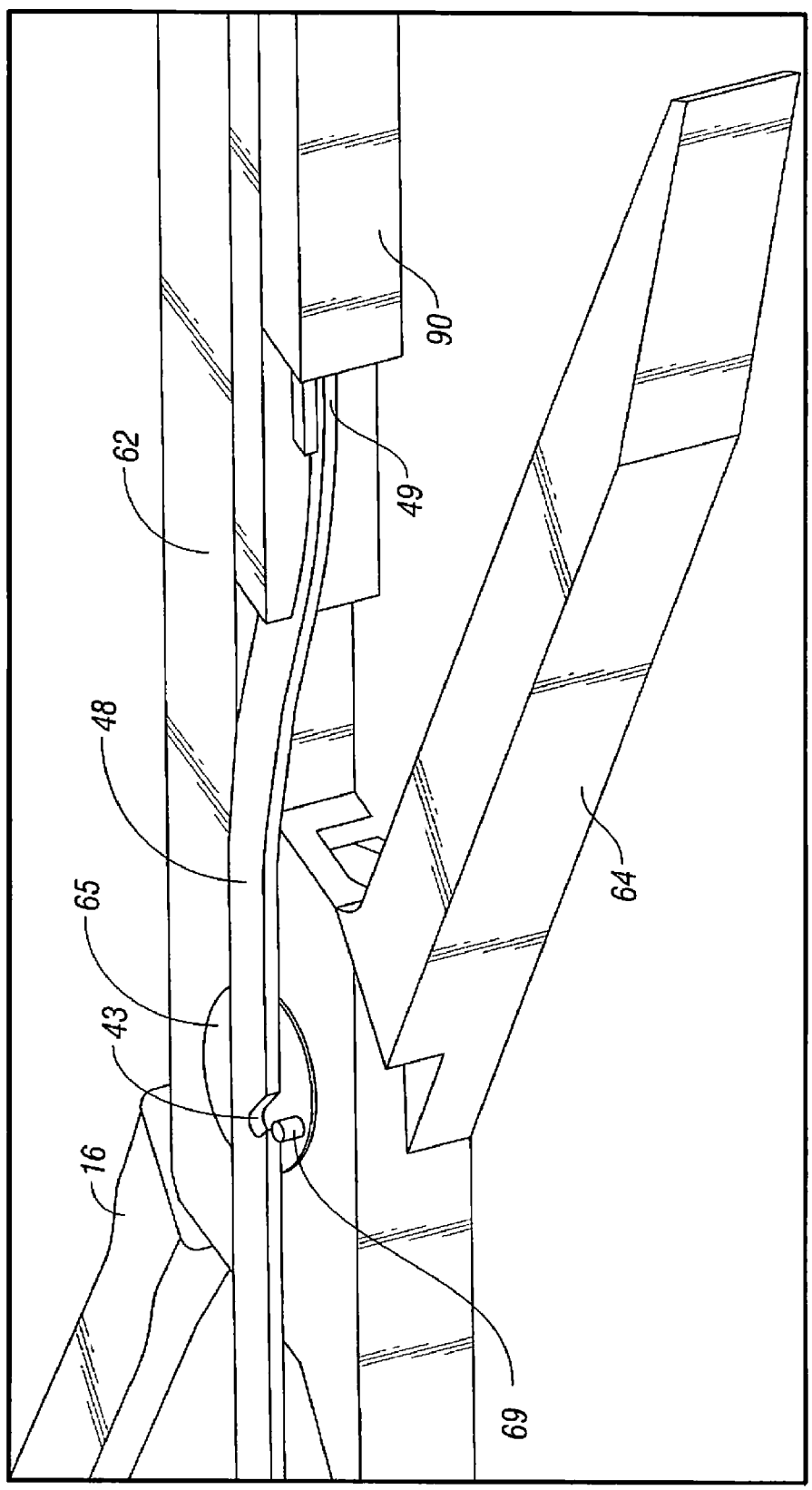
FIG. 1E is an enlarged, perspective view showing the distal end of the actuating mechanism which attaches to the cutting knife.

As best seen in FIGS. 1C and 1D, the jaw members 62 and 64 include a knife channel 69 disposed therebetween which is configured to allow reciprocation of a cutting mechanism 90 therewithin. One example of a knife channel is disclosed in commonly-owned U.S. patent application Ser. No. 10/284,562 the entire contents of which are hereby incorporated by reference herein. Preferably, the complete knife channel 69 is formed when two opposing channel halves 69a and 69b come together upon grasping of the tissue. It is envisioned that the knife channel 69 may be tapered or some other configuration which facilitates or enhances cutting of the tissue during reciprocation of the cutting mechanism 90 in the distal direction. Moreover, the knife channel 69 may be formed with one or more safety features which prevent the cutting mechanism 90 from advancing through the tissue until the jaw members 62 and 64 are closed about the tissue.

FIG. 1B shows a lockout mechanism 47 associated with the actuating assembly 40 to prevent advancement of the cutting mechanism until the jaw members are positioned about tissue. Other lockout mechanisms and features are described in commonly-owned U.S. application Ser. Nos. 10/460,926, 10/461,550 and 10/462,121 which are all incorporated by reference herein in their entirety. FIGS. 6A-6D show another example of a safety/lockout mechanism.

As best shown in FIGS. 1A-1D, the arrangement of shaft 12 is slightly different from shaft 20. More particularly, shaft 20 is hollow to define a chamber 28 therethrough which is dimensioned to house both the handswitch 50 (and the electrical components associated therewith as explained in more detail below) and the actuating mechanism 40. As best seen in FIGS. 1C and 1D, the actuating mechanism 40 includes a finger tab 42 which is operatively associated with a first gear rack 44 such that movement of the finger tab 42 moves the first rack 44 in a corresponding direction. The actuating mechanism 40 also includes a second gear rack 46 which is operatively associated with a drive rod 48 which advances the cutting mechanism 90 as will be explained in more detail below. Drive rod 48 includes a distal end 49 which is configured to mechanically support the cutting mechanism 90 (See FIG. 1E).

Distal end 49 may include one or more guide mechanisms (not shown) to control or guide the cutting mechanism 90 through the knife channel 69 between opposing jaw members 62 and 64. Preferably, the drive rod 48 is made from a flexible wire or plastic sheath which does not buckle upon forward movement thereof. It is also contemplated that the drive rod may include a groove or notch 43 which prevents movement thereof when the jaw members are opened relative to one another. Likewise, pivot 65 (or some other part of forceps 10) may include a corresponding detent or protrusion 69' which engages the notch 43 to prevent accidental firing of the cutting mechanism 90 when the forceps 10 is disposed in the open position.

Interdisposed between the first and second gear racks 44 and 46, respectively, is a pinion gear 45 which mechanically meshes with both gear racks 44 and 46 and converts proximal motion of the finger tab 42 into distal translation of the drive rod 48 and vice versa. More particularly, when the user pulls the finger tab 42 in a proximal direction within a predisposed channel 29 in the chamber 28 as represented by arrow "A", the first rack 44 is translated proximally which, in turn, rotates the pinion gear 45 in a clockwise direction. Rotation of the pinion gear 45 in a clockwise direction forces the second rack 46 to translate the drive rod 48 distally (See arrow "B") which advances the cutting mechanism 90 through tissue grasped between jaw members 62 and 64. As mentioned above, the cutting mechanism 90, e.g., knife, blade, wire, etc., is advanced through channel 69 upon distal translation of the drive rod 48.

It is envisioned that multiple gears or gears with different gear ratios may be employed to reduce surgical fatigue which may be associated with advancing the cutting mechanism 90. In addition, it is contemplated the tracks 44 and 46 may be of different length to provide additional mechanical advantage for advancing the jaw members through tissue. As best shown in FIG. 1C, the rack and pinion arrangement may be curved for spatial purposes and to facilitate handling and/or to enhance the overall ergonomics of the forceps 10.

A spring 85 may be employed within chamber 28 to bias the first rack 44 upon proximal movement thereof such that upon release of the finger tab 42, the force of the spring 85 automatically returns the first rack 44 to its distal most position within channel 29. Obviously, spring 85 may be operatively connected to bias the second rack 46 to achieve the same purpose.

Preferably, the finger tab 42 includes one or more ergonomically friendly features which enhance the tactile feel and grip for the user to facilitate actuation of the finger tab 42. Such features may include, raised protuberances, rubber inserts, scallops and gripping surfaces and the like.

FIG. 1D shows another embodiment of the present disclosure similar to the embodiment of FIG. 1C which includes a ratchet 74 for selectively locking the jaw members 62 and 64 relative to one another at various positions during pivoting. A first ratchet interface 76 extends from the proximal end 14 of shaft member 12 towards a second ratchet interface 78 on the proximal end 24 of shaft 20 in a generally vertically aligned manner such that the inner facing surfaces of each ratchet 76 and 78 abut one another upon closure about the tissue. Preferably, each ratchet interface 76 and 78 includes a plurality of flanges 77a and 77b, respectively, which project from the inner facing surface of each ratchet interface 76 and 78 such that the ratchet interfaces 77a and 77b interlock in at least one position. In the embodiment shown in FIG. 1D, the ratchet interfaces 77a and 77b interlock at several different positions.

Preferably, each position associated with the cooperating ratchet interfaces 77a and 77b holds a specific, i.e., constant, strain energy in the shaft members 12 and 20 which, in turn, transmits a specific closing force to the jaw members 62 and 64. It is envisioned that the ratchet 74 may include graduations or other visual markings which enable the user to easily and quickly ascertain and control the amount of closure force desired between the jaw members.

FIG. 1D also shows a lockout mechanism 99 which is designed to prevent firing of the cutting mechanism until the jaw members 62 and 64 are moved into closed position about tissue. As can be appreciated, the lockout 99 acts as a safety mechanism to prevent accidental severing of tissue prior to formation of a tissue seal. It is also envisioned that the lockout could cooperate with one or more electrical or electromechanical sensors (not shown) which prevent the cutting mechanism 90 from advancing through tissue until a tissue seal has been created. For example, the lockout 99 could include a sensor which upon completion of a tissue seal activates a switch or release (not shown) which unlocks the cutting mechanism 90 for advancement through tissue.

It is envisioned that by making the forceps 10 disposable, the forceps 10 is less likely to become damaged since it is only intended for a single use and, therefore, does not require cleaning or sterilization. As a result, the functionality and consistency of the vital sealing components, e.g., the conductive surfaces 67 and 68, the stop member(s) 150, and the insulative housings 63 and 66 will assure a uniform and quality seal.

FIGS. 2A-2E show another embodiment of the presently disclosed forceps 100 which includes an alternative actuating mechanism 140 which selectively advances the cutting mechanism 190 to separate the tissue once sealed. More particularly, forceps 100 includes shafts 112 and 120 which cooperate to move jaw members 162 and 164 from a first position wherein the jaw members 162 and 164 are disposed in spaced relation relative to one another to a second position wherein the jaw members cooperate to grasp tissue therebetween. Much like the forceps 10 of FIGS. 1A-1C, shaft 112 and shaft 120 are dimensioned to allow reciprocation of shaft 112 within the elongated channel 121 of shaft 120. In addition, jaw members 162 and 164 are similar to the jaw members 62 and 64 of FIGS. 1A-1C and include similar elements and features, e.g., sealing surfaces 167 and 168, outer insulative housings 163 and 166 and pivot 165. Forceps 100 also includes ring handles 115 and 117 which each define a corresponding finger hole 115a and 117a, respectively, therein to enable the user to manipulate and grasp tissue with the jaw members 162 and 164.

Ring handle 117 includes an elongated drive path 119 defined therethrough which extends from the chamber 129, around the ring handle 117 and through the shaft 120 to the distal end of the forceps 100. As best seen in FIGS. 2B and 2C the finger tab 142 is slideable within channel 129 in a proximal direction (represented by arrow "A") which advances the cutting mechanism 90 through tissue held between jaw members 162 and 164. More particularly, the finger tab 142 is connected to a sled-like carrier 144 which is operatively connected to a flexible element 148 such that movement of the carrier 144 moves the element 148. Element 148, in turn, is reciprocated within the drive path 119 and extends around the handle 117 to the distal end 116 where the distal end 149 mechanically engages the cutting mechanism 90. As can be appreciated, proximal movement of the finger tab 142 moves the flexible element 148 within the drive path 119 around the handle 117 which distally advances the cutting mechanism 90 through tissue. It is envisioned that designing the forceps 100 to have the driving flexible element 148 advance around the ring handle 117 provides maximum spatial benefit and facilitates handling of the forceps 100. A spring 185 may be employed to bias the finger tab 142 in a distal-most position and automatically return the finger tab 142 after deployment.

It is envisioned that the actuating mechanism 140 could be configured utilizing one or more pulleys 225 (See FIG. 2E) to facilitate translation of the flexible element 148 through the tissue. In addition, it is contemplated that the actuating mechanism 140 can be configured such that distal movement of the finger tab 142 advances the flexible element 148 in a distal direction to cut tissue utilizing one or more pulleys (See FIG. 2E).

FIG. 2C preferably utilizes a flexible plastic sheath or flexible linkage as the flexible element 148 to advance the cutting mechanism 90. It is envisioned that the flexible linkage prevents buckling during activation. However and as best seen in FIG. 2D, a flexible wire may be utilized in lieu of the flexible plastic sheath. Wire 248 operates in a similar fashion as the plastic flexible sheath 148 of FIG. 2C such that upon movement of the finger tab 142 the flexible wire 248 advances the cutting mechanism 90 through tissue held between jaw members 162 and 164.

FIGS. 5A-5C show the electrical details relating to the switch 50. More particularly and as mentioned above, cable 70 includes three electrical leads 70a, 70b and 70c which are fed through shaft 20. The electrosurgical cable 70 is fed into the bottom of shaft 20 and is held securely therein by one or more mechanical interfaces (not shown). Lead 70c extends directly from cable 70 and connects to jaw member 64 to conduct the second electrical potential thereto. Leads 70a and 70b extend from cable 70 and connect to the hand switch or joy-stick-like toggle switch 50 (or 150 in FIG. 2A).

Figure 2A:
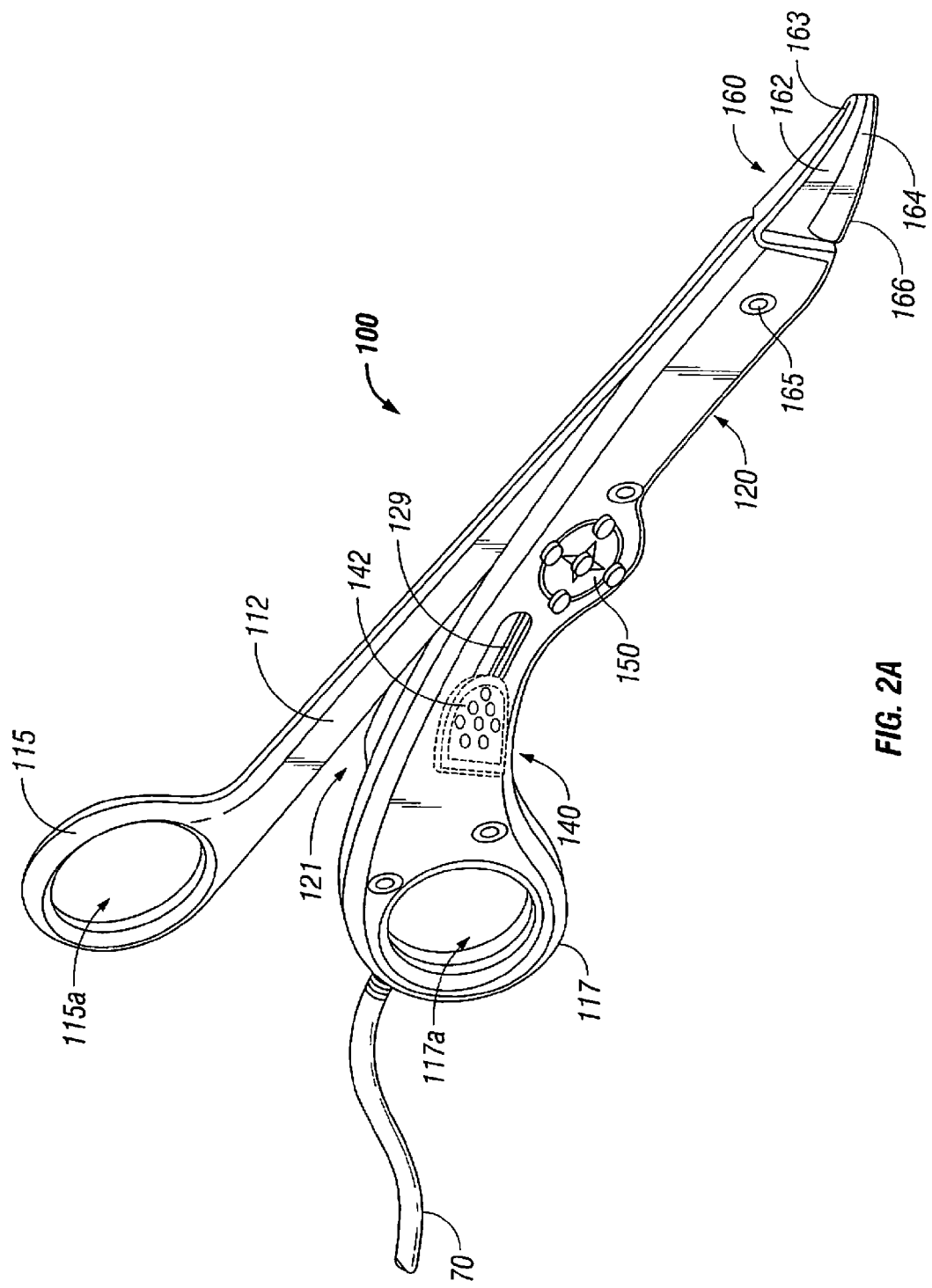
FIG. 2A is a left, perspective view of an alternate embodiment of an open forceps according to the present disclosure.
Figure 2B:
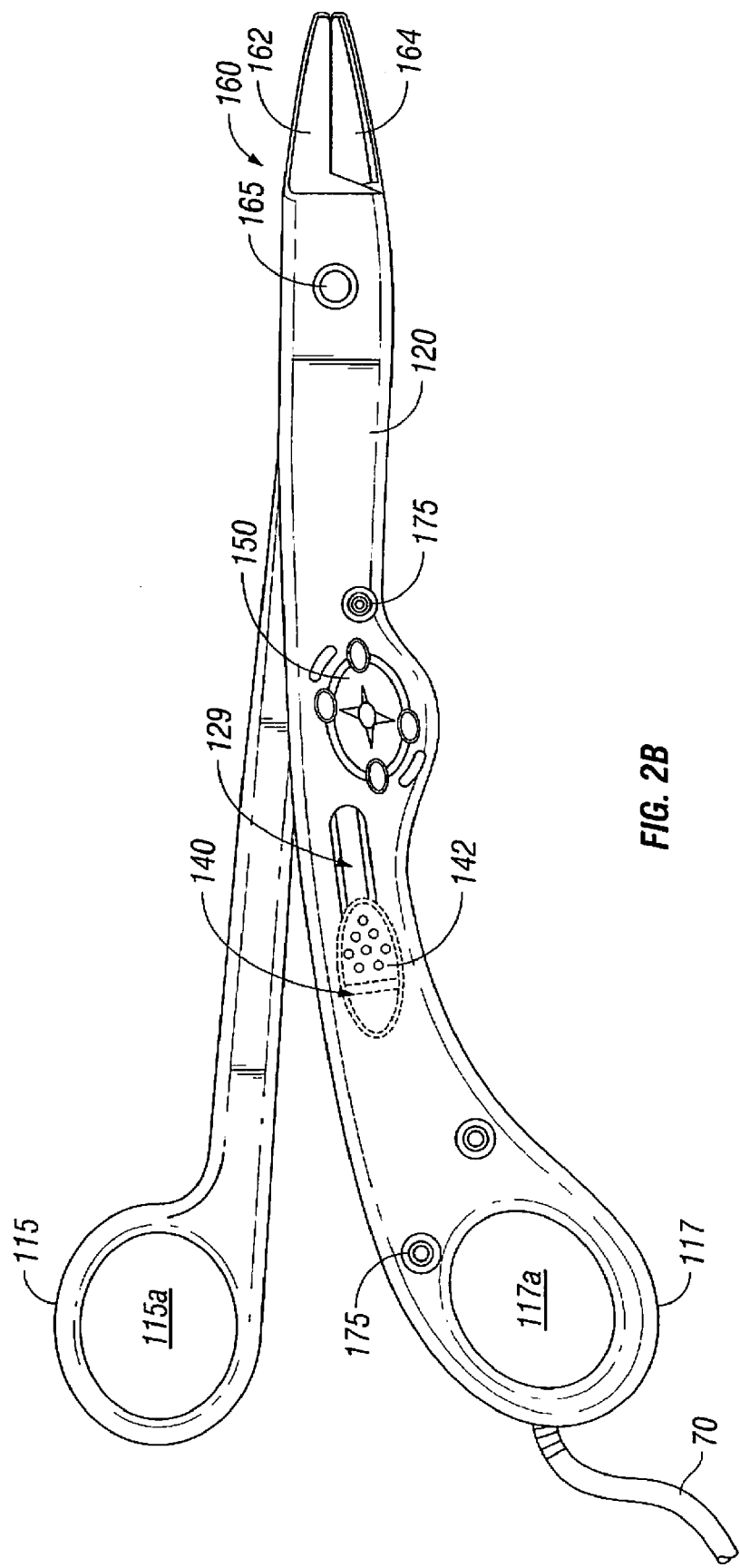
FIG. 2B is a left, side view of the forceps of FIG. 2A.
Figure 2C:
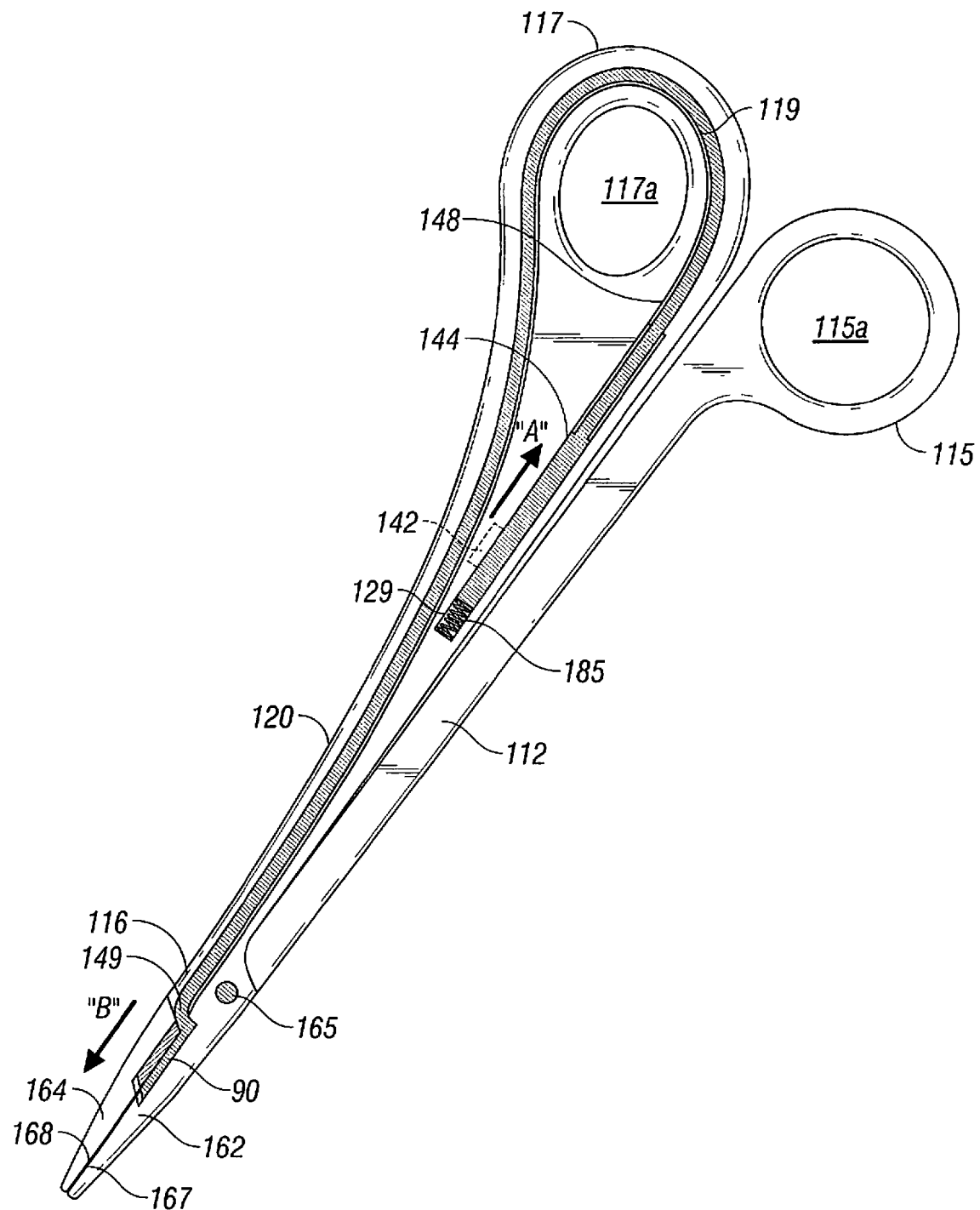
FIG. 2C is an internal view of the forceps of FIG. 2A showing a flexible linkage actuating mechanism for advancing the cutting knife.
Figure 2D:
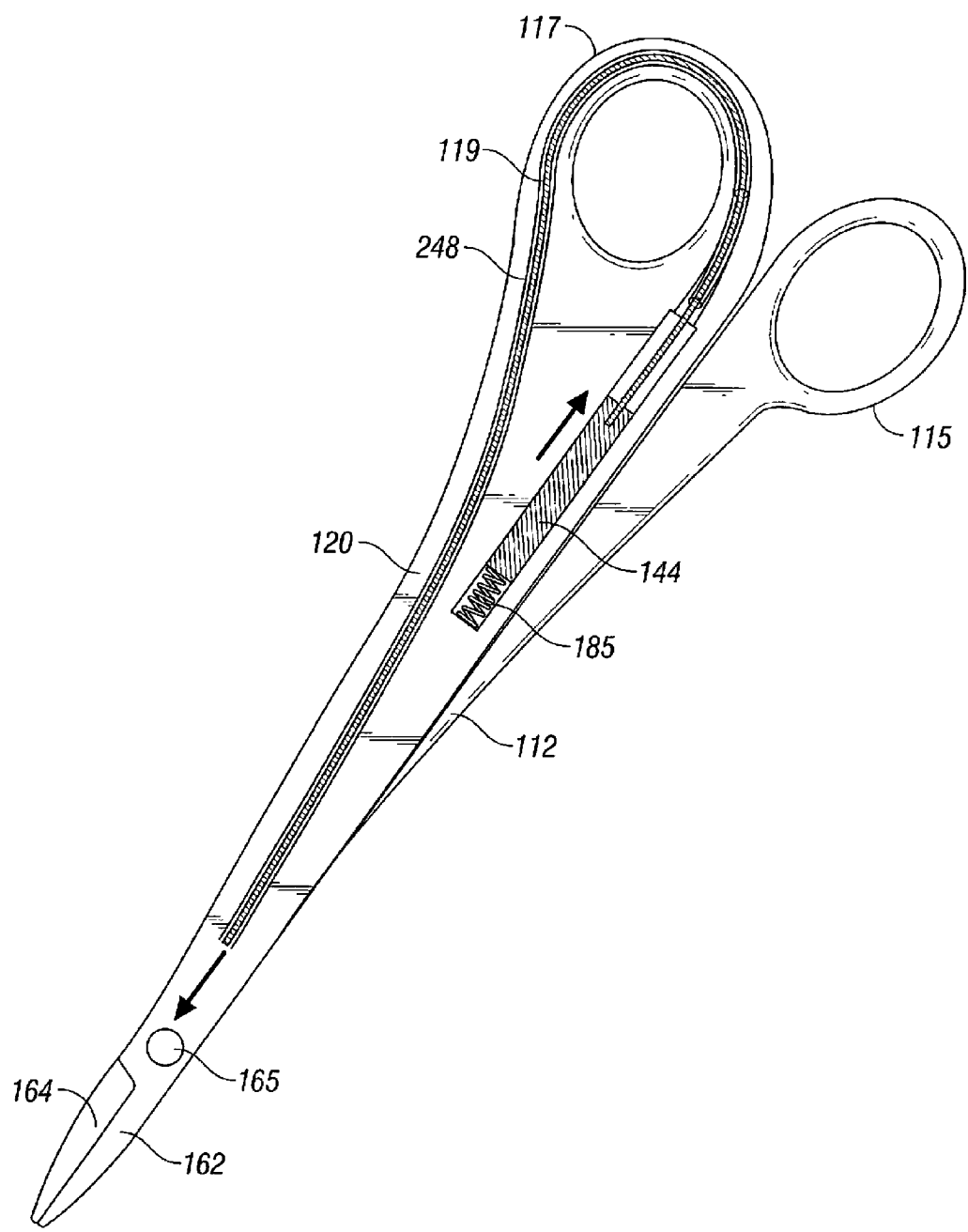
FIG. 2D is an internal view of the forceps of FIG. 2A showing a flexible wire actuating mechanism for advancing the cutting knife.
Figure 2E:
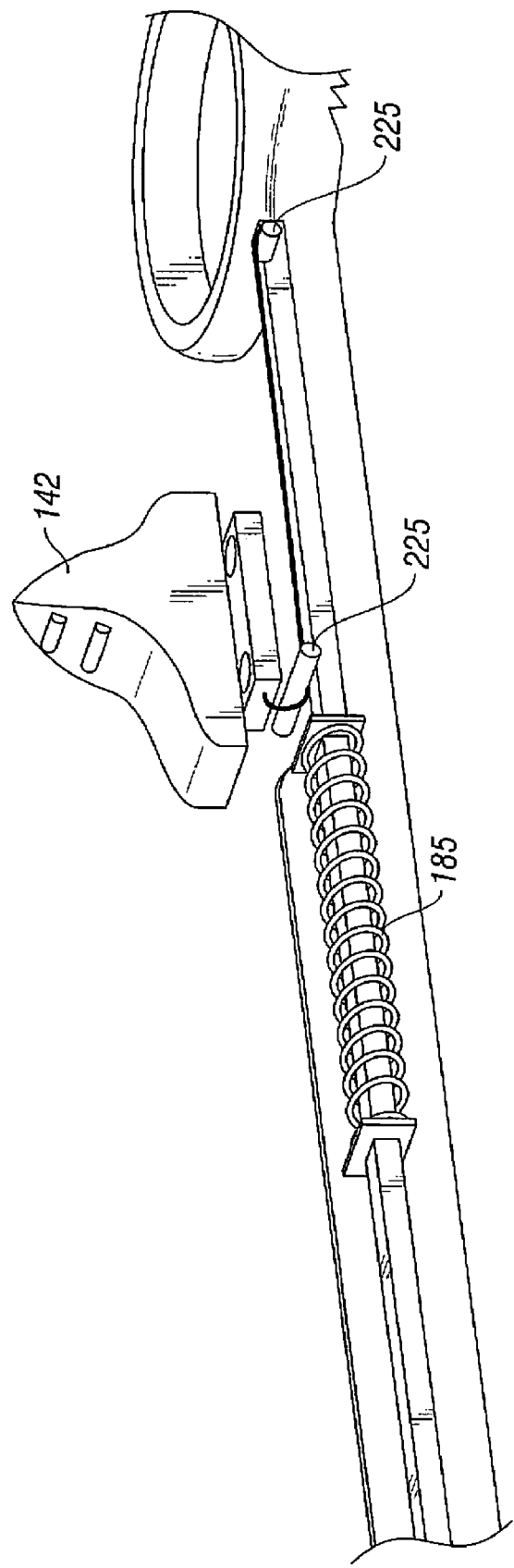
FIG. 2E is a side, internal view of the trigger for advancing and retracting the flexible wire of FIG. 2D.

Several different types of handswitches 50 are envisioned, for example, switch 50 is a regular push-button style switch while switch 150 of FIG. 2A is more like a toggle switch. It is envisioned that a toggle switch 150 permits the user to selectively activate the forceps 10 in a variety of different orientations, i.e., multi-oriented activation, which simplifies activation. One particular type of handswitch is disclosed in commonly-owned, co-pending U.S. patent application Ser. No. 10/460,926 the contents of which are hereby incorporated by reference herein.

The electrical leads 70a and 70b are electrically connected to the switch 50 (or 150). When the switch 50 is depressed, a trigger lead 71 carries the first electrical potential from the switch 50 to jaw member 62. As mentioned above, the second electrical potential is carried by lead 70c directly from the generator (not shown) to jaw member 64. It is envisioned that a safety switch or circuit (not shown) may be employed such that the switch 50 cannot fire unless the jaw members 62 and 64 are closed and/or unless the jaw members 62 and 64 have tissue held therebetween. In the latter instance, a sensor (not shown) may be employed to determine if tissue is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. Various sensor mechanisms and feedback systems are described in commonly-owned, co-pending U.S. patent application Ser. No. 10/427,832 the entire contents of which are hereby incorporated by reference herein.

Preferably, the jaw members 62 and 64 are electrically isolated from one another such that electrosurgical energy can be effectively transferred through the tissue to form a tissue seal. Preferably, each jaw member, e.g., 62, includes a uniquely-designed electrosurgical cable path disposed therethrough which transmits electrosurgical energy to the electrically conductive sealing surface 67. It is envisioned that jaw member 62 may include one or more cable guides or crimp-like electrical connectors to direct cable lead 71 towards electrically conductive sealing surface 67. Preferably, cable lead 71 is held loosely but securely along the cable path to permit pivoting of the jaw member 62 about pivot 65.

As best shown in FIGS. 5B and 5C, the cable leads 70a, 70b and 70c are protected by two insulative layers, an outer protective sheath 76 which surrounds all three leads 70a, 70b and 70c and a secondary protective sheath 75a, 75b and 75c which surrounds each individual cable lead, 70a, 70b and 70c, respectively. The two electrical potentials are isolated from one another by virtue of the insulative sheathing surrounding each cable lead 70a, 70b and 70c.

Figure 3:
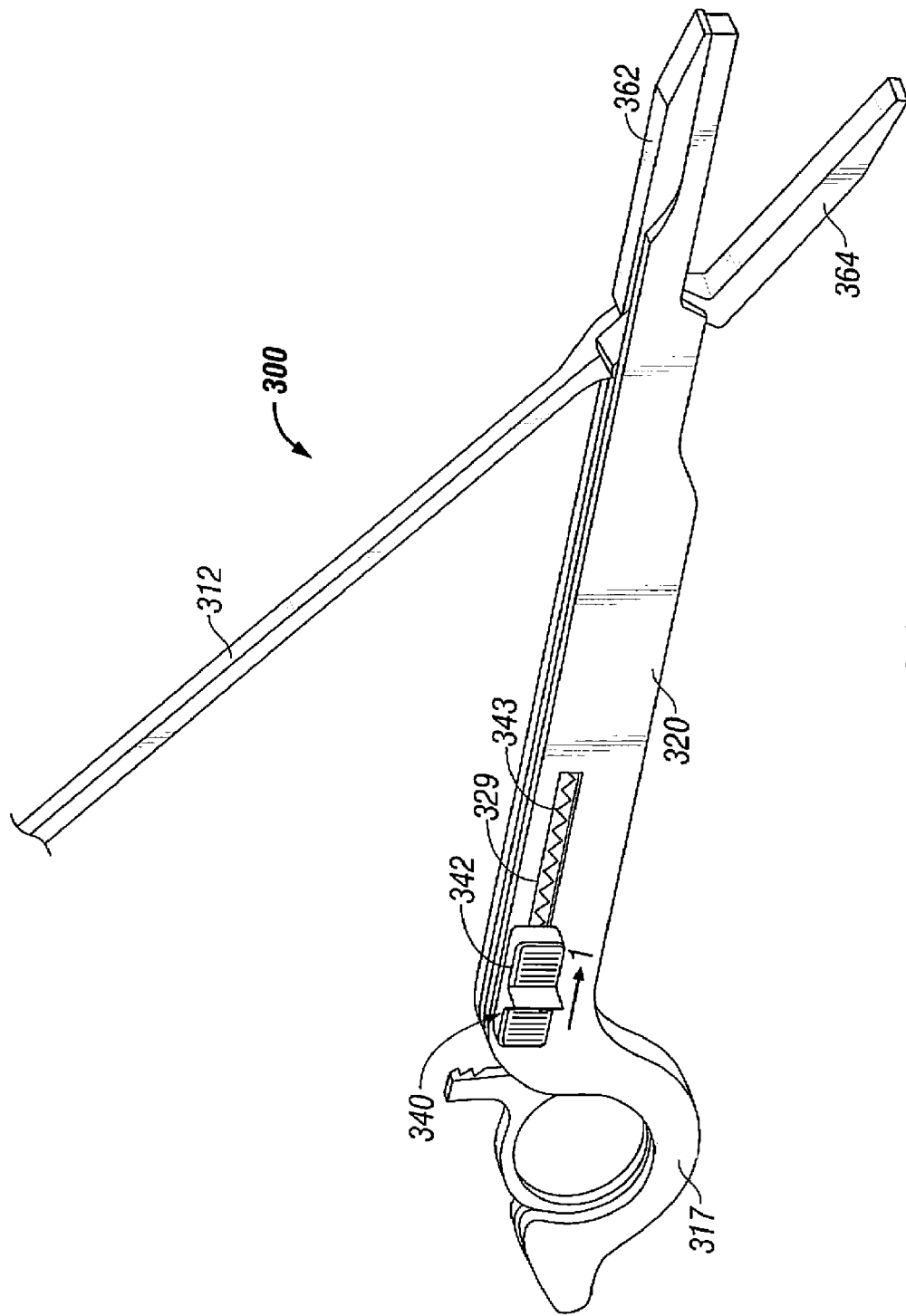
FIG. 3 is a perspective view of an alternate embodiment of the open forceps according to the present disclosure having a forwardly activateable actuating mechanism for advancing the cutting knife.

FIG. 3 shows yet another embodiment of the forceps 300 according to the present disclosure wherein the actuating mechanism 340 includes a slide switch 342 which advances the cutting mechanism 90 (not shown in this figure) through tissue grasped between opposing jaw members 362 and 364. More particularly, the slide switch 342 is pushed distally within channel 329 disposed in the shaft 320 by the surgeon to selectively sever tissue once sealed. The switch 342 may include a bias member or spring 343 which automatically returns the cutting mechanism once advanced in a distal direction, i.e., automatic return. Other biasing members are also contemplated which are known in the art, e.g., elastomeric bands, pulleys, etc.

Alternatively, the actuating mechanism 340 may be spring-loaded and advanced automatically when switch 342 is depressed by the surgeon. After deployment, the surgeon manually retracts the switch 342 to reset the switch 342 and cutting mechanism 90 for subsequent deployment.

Figure 4:
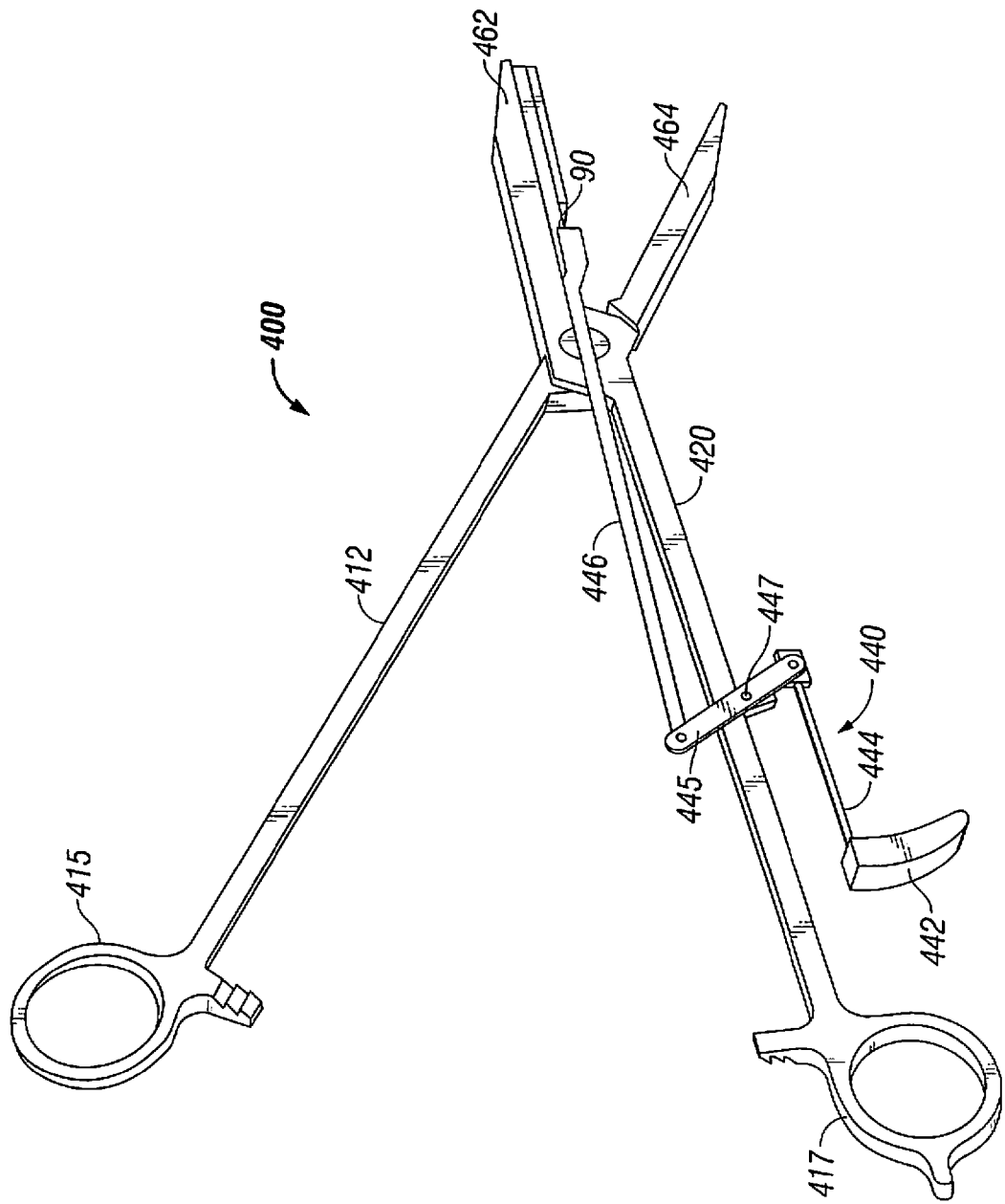
FIG. 4 is a perspective view of an alternate embodiment of the open forceps according to the present disclosure having a lever arm which advances the cutting knife.

FIG. 4 shows yet another embodiment of the presently disclosed forceps 400 which includes a lever-like actuator 440 which is designed to advance the cutting mechanism 90 through tissue grasped between jaw members 462 and 464. More particularly, actuating mechanism 440 includes a finger tab 442 which is positioned for actuation by the user and which is connected to a proximal end of a first link 444. Link 444 is, in turn, connected at a distal end thereof to one end of a pivot lever 445. Pivot lever 445, in turn, is connected at the opposite end thereof to a second link 446 which connects to the cutting mechanism 90.

Pivot lever 445 is rotatably connected about a pivot pin 447 to shaft 420 such that movement of the finger tab 442 and link 444 in a proximal direction distally advances link 446 in a distal direction to move the cutting mechanism 90 through tissue. A spring (not shown) may be included to automatically return the finger tab 442 to its distal-most position after cutting. Alternatively, a third ring handle (not shown) may be employed in lieu of the finger tab 442 to advance link 444 to actuate the pivot lever 445.

As mentioned above, the knife channel 69 may be formed with a lockout or one or more other safety features which prevent the knife 90 from advancing through the tissue until the jaw members 62 and 64 are closed about the tissue. As best seen in FIGS. 6A-6D, one possible lockout or safety mechanism 505 is envisioned which both prevents actuation of the cutting blade 90 when the jaw members 62 and 64 are disposed in an open configuration and also prevents opening of the jaw members 62 and 64 when the actuating mechanism 40 is being deployed to advance the cutting blade 90.

More particularly, the shaft 520 and respective handle 517 may be configured to include an elongated channel 529 disposed therethrough which allows reciprocation of a safety bar 527 therein. Although shown as generally an elongated channel, it is envisioned that the channel 529 may be circular or curved to accomplish the same purpose. Channel 529 is composed of two channel halves 529a and 529b disposed in horizontal registry with one another and which are separated by an opening 537 therebetween.

A leaf spring 525 (or the like) is disposed within a chamber 523 defined in the handle 517 and is moveable within the chamber 523 from a first position wherein the spring 525 is biased to block opening 537 to a second position wherein the spring 525 is forced out of opening 537 to allow reciprocation of the safety bar 527. Handle 515 includes a flange 513 which extends upwardly towards handle 517 and which includes an aperture 519 defined therein which is dimensioned to receive the safety bar 527 therethrough. The flange 513 is designed to be in vertical registration with opening 537.

Figure 6A:
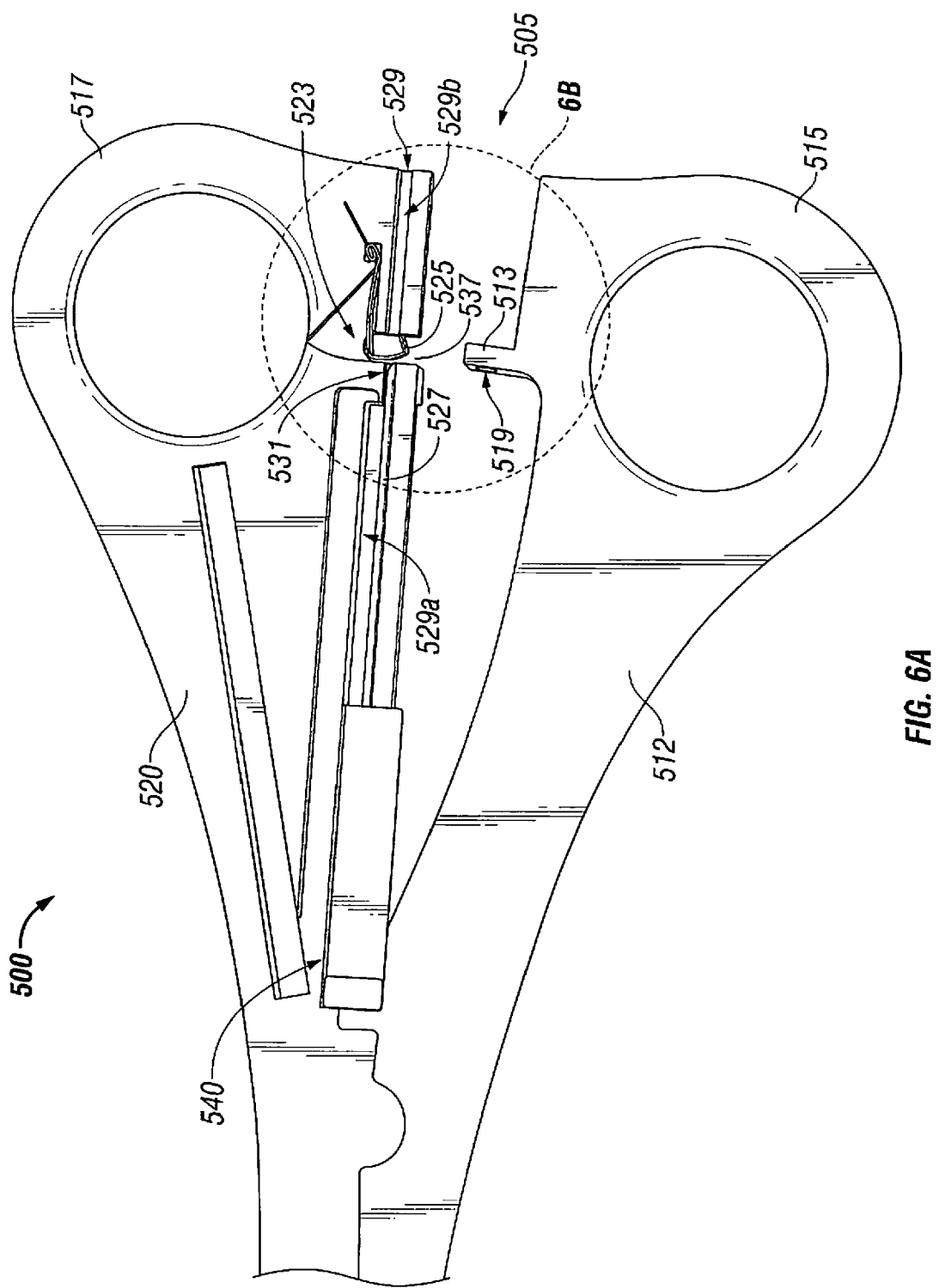
FIG. 6A is an enlarged view of a safety mechanism according to the present disclosure shown in a disengaged position.
Figure 6B:
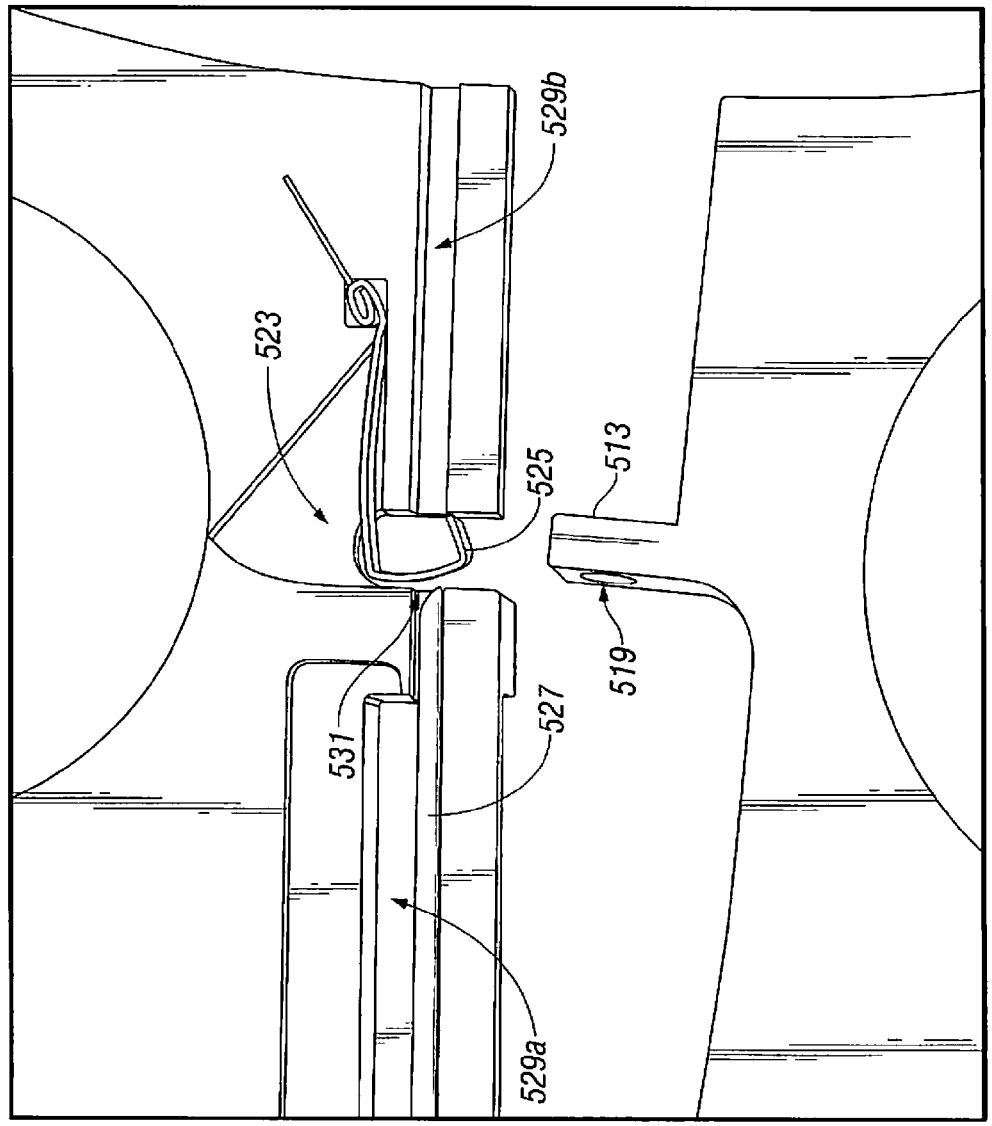
FIG. 6B is a greatly-enlarged view of the safety mechanism of FIG. 6A.
Figure 6C:
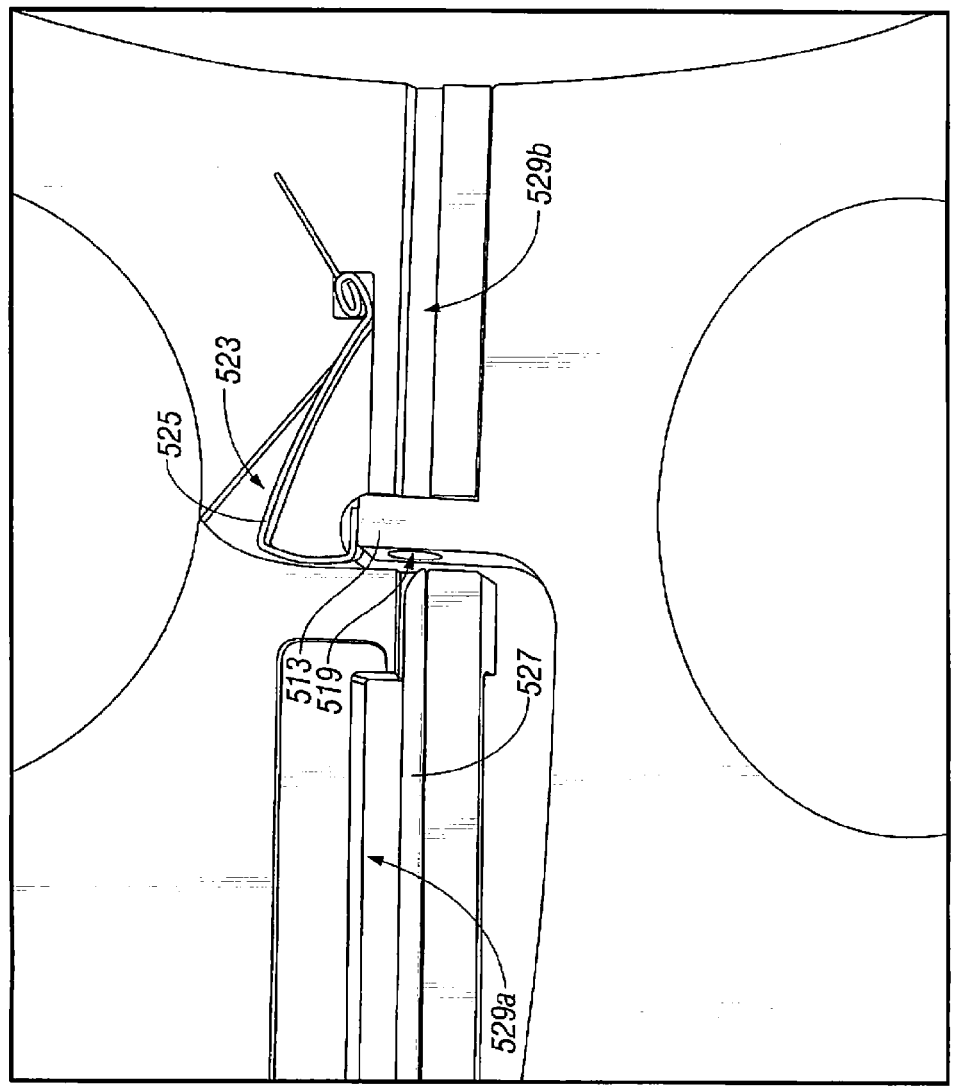
FIG. 6C is a greatly-enlarged view of the safety mechanism of FIG. 6A shown being activated.
Figure 6D:
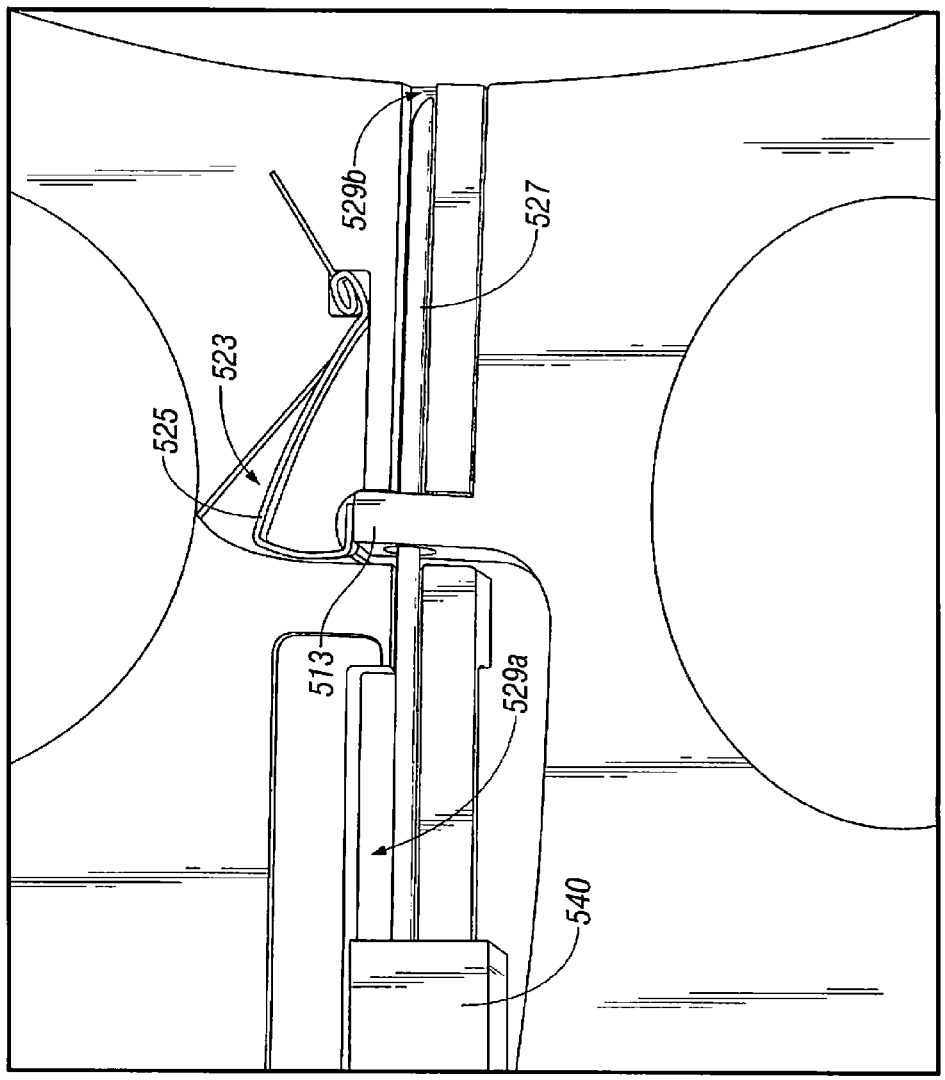
FIG. 6D is a greatly-enlarged view of the safety mechanism of FIG. 6A in an activated position to allow reciprocation of the actuating mechanism.

In use, as the jaw members 62 and 64 grasp tissue (move from the first to second positions), the flange 513 is forced into opening 537 to dislodge the spring 525 out of the opening 537 and into chamber 523. When the spring 525 is at least substantially incorporated into chamber 523, the aperture 519 will align with the elongated channels 529a and 529b (See FIG. 6C). As mentioned above, a ratchet may be employed to hold the two handles 515 and 517 together with the appropriate closure force for sealing tissue. At this point, the user is free to activate the actuating mechanism 40 to advance the cutting blade 90 which as best seen in FIG. 6D translates the safety bar 527 proximally and through aperture 513 and into elongated channel 529b. As can be appreciated, the user is prevented from advancing the cutting blade 90 until the jaw members 62 and 64 are closed about tissue. Moreover, when the actuating mechanism 40 is activated, the handles 515 and 517 are locked and cannot be opened until the actuating mechanism 40 is released.

Figure 6E:
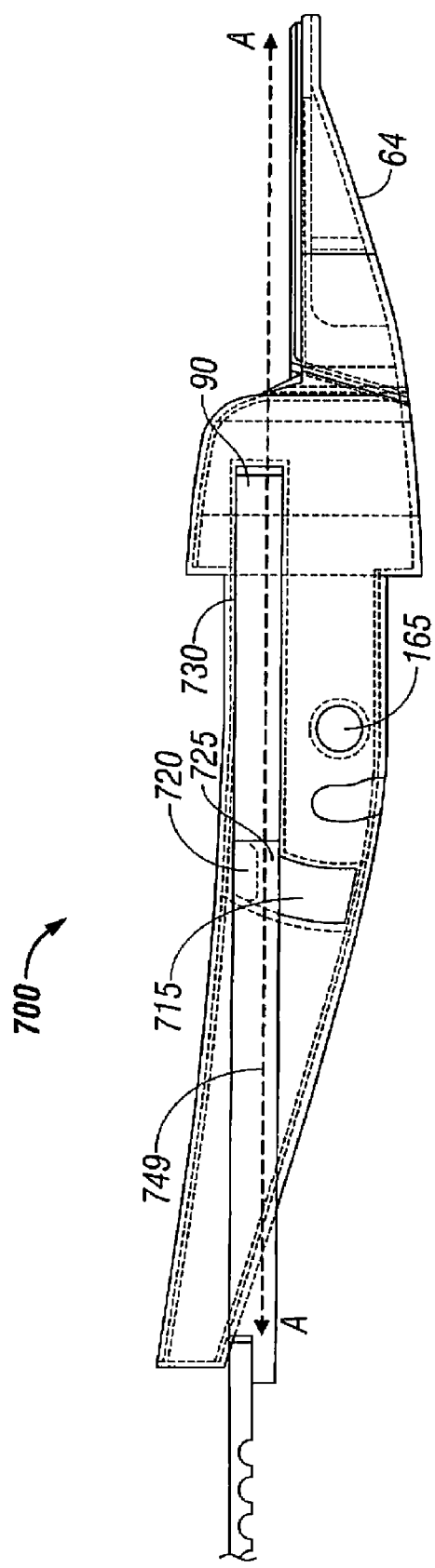
FIG. 6E is a greatly-enlarged view of another embodiment of a safety mechanism or lockout which may be utilized with any of the above embodiments of the open forceps described above.
Figure 6F:
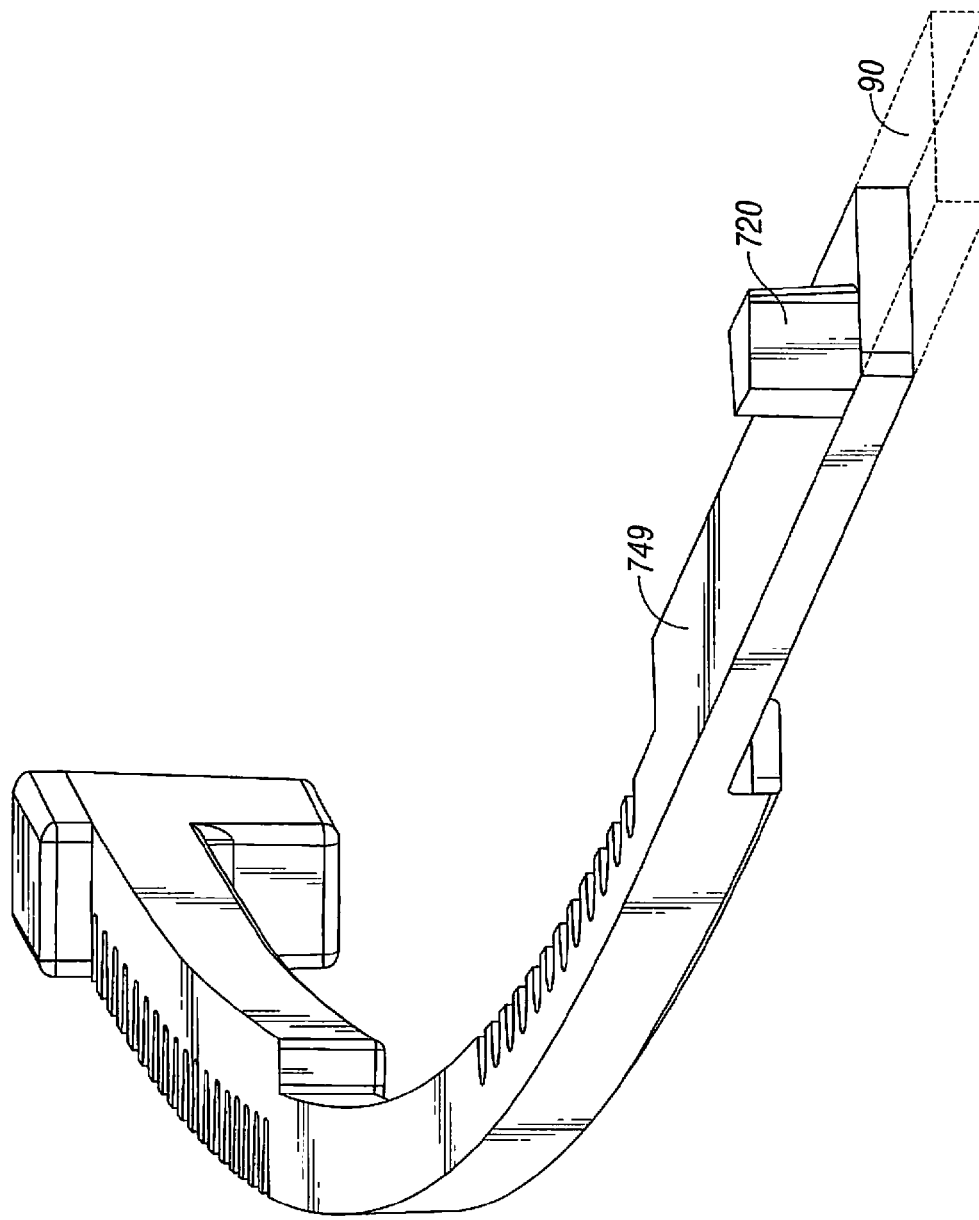
FIG. 6F is a greatly-enlarged view of a knife carrier for use with the safety mechanism of FIG. 6E.

FIGS. 6E and 6F show another version of a safety or lockout mechanism 700 which acts to prevent the cutting blade 90 from being distally activated when the forceps is disposed in an open configuration, i.e., the jaw members 62 and 64 are spaced relative to one another. More particularly, lockout mechanism 700 is designed of two components which mechanically cooperate to prevent accidental blade advancement, namely, a cutting blade carrier 749 and a blade lockout slot 715. Cutting blade carrier 749 is configured to mechanically support the cutting blade 90 for advancement through tissue held between the jaw members 62 and 64 and preferably includes a detent or protrusion 720 which extends from at least one side thereof. The lockout slot 715 is preferably disposed in a proximal portion of jaw member 64 near the jaw pivot 165.

When the jaw members 62 and 64 are closed about tissue, the detent 720 is freely extendible within a blade slot 730 disposed within at least one of the jaw members, e.g., jaw member 64, to cut tissue. Preferably, a return spring (not shown) automatically returns the cutting blade 90 once the user releases the actuator 40. When the jaw members 62 and 64 are disposed in an open configuration, the detent 720 rotates into lockout slot 715 thus preventing distal reciprocation of the cutting blade 90 when the actuator 40 is actuated. A guide notch 725 may be positioned within slot 730 to facilitate entry of the detent 720 into lockout slot 715.

Figure 7:
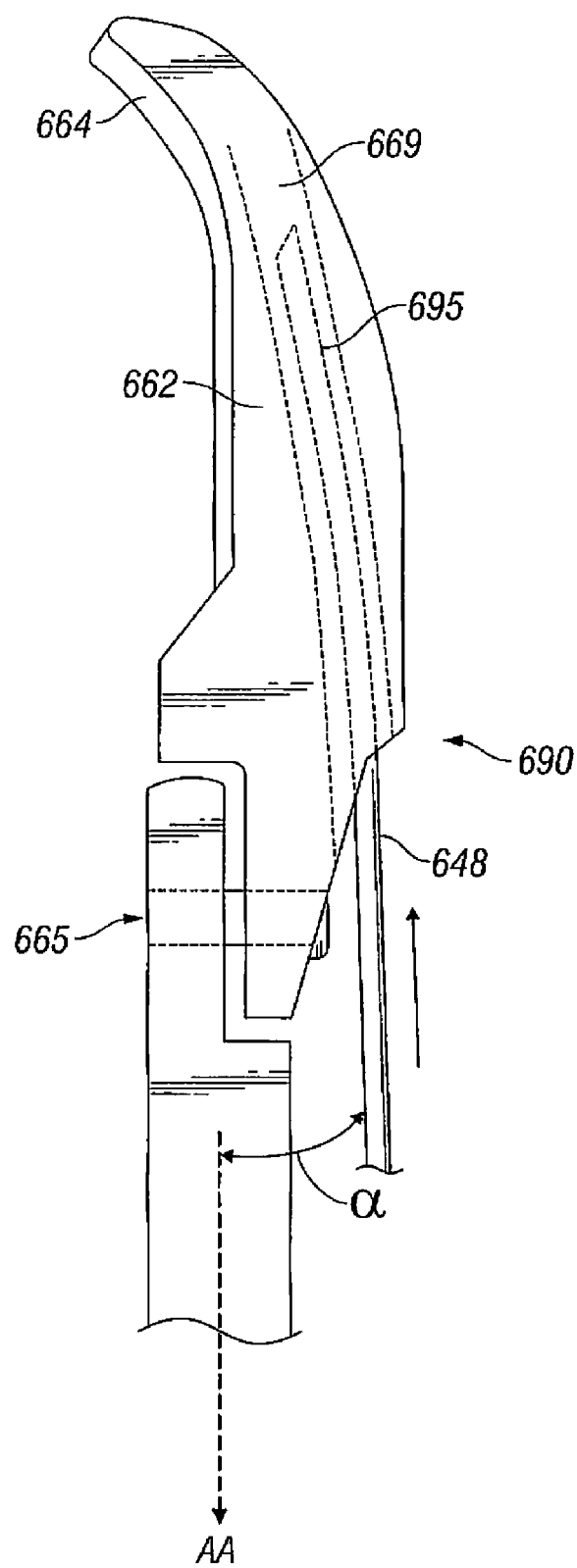
FIG. 7 is an enlarged, top view showing a cutting knife which is generally disposed off-axis relative to the distal end of the forceps to facilitate tissue cutting around a curved jaw member.

FIG. 7 shows an alternate embodiment of the cutting mechanism 690 which is distally advanceable to cut tissue disposed between the jaw members 662 and 664. More particularly, cutting mechanism 690 is designed to include a cutting blade 695 which is distally advance above by a drive rod 648 through a curved knife slot 669 disposed between jaw members 662 and 664. The drive rod 648 and the cutting blade 695 are positioned slightly off-axis to allow for blade 695 to easily move within curved slot 669. In other words, the distal end of the instrument includes a longitudinal axis "AA" defined therethrough and the drive rod 648 is positioned at an angle a relative to the longitudinal axis "AA". As can be appreciated, positioning the drive rod "off-axis" enables the cutting blade 695 to move more easily move through the knife channel 669 to cut tissue disposed between the jaw members 662 and 664. It is envisioned that the jaw members 662 and 664 and/or the drive rod 648 may include a safety which prevents the blade 695 from reciprocating in the knife channel 669 when the jaw members 662 and 664 are disposed in an open configuration about pivot 665.

In operation, the surgeon simply utilizes the two opposing handle members 15 and 17 to approximate and grasp tissue between jaw members 62 and 64. The surgeon then activated the handswitch (or footswitch if applicable) to provide electrosurgical energy to each jaw members to communicate energy through the tissue held therebetween. Once sealed the surgeon activates the actuating mechanism 40 to advance the cutting blade 90 through the tissue to sever the tissue along the tissue seal.

From the foregoing and with reference to the various figure drawings, those skilled in the art will appreciate that certain modifications can also be made to the present disclosure without departing from the scope of the same. For example, although the electrical connections are preferably incorporated within one shaft 20 and the forceps is intended for right-handed use, it is contemplated the electrical connections may be incorporated within the other shaft 12 depending upon a particular purpose and/or to facilitate manipulation by a left-handed user.

It is also contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue grasped between the jaw members 62 and 64. The sensor or feedback mechanism may also measure the impedance across the tissue during sealing and provide an indicator (visual and/or audible) that an effective seal has been created between the jaw members 62 and 64. Commonly-owned U.S. patent application Ser. No. 10/427,832 discloses several different types of sensory feedback mechanisms and algorithms which may be utilized for this purpose. The contents of this application are hereby incorporated by reference herein.

Experimental results suggest that the magnitude of pressure exerted on the tissue by the sealing surfaces of the jaw members 62 and 64 are important in assuring a proper surgical outcome. Tissue pressures within a working range of about 3 $kg/cm^2$ to about 16 $kg/cm^2$ and, preferably, within a working range of 7 $kg/cm^2$ to 13 $kg/cm^2$ have been shown to be effective for sealing arteries and vascular bundles. Tissue pressures within the range of about 4 $kg/cm^2$ to about 6.5 $kg/cm^2$ have proven to be particularly effective in sealing arteries and tissue bundles.

In one embodiment, the shaft 12 and 20 are manufactured such that the spring constant of the shaft portions 12a and 12b, in conjunction with the placement of the ratchet interfaces 32a and 32b, will yield pressures within the above working range. In addition, the successive positions of the ratchet interfaces increase the pressure between opposing sealing surfaces incrementally within the above working range.

It is also envisioned that the drive rod 48 may be connected to the same or alternate source of electrosurgical energy and may be selectively energizable by the surgeon during cutting. As can be appreciated, this would enable the surgeon to electrosurgically cut the tissue along the tissue seal. As a result thereof, a substantially dull blade may be employed to electrosurgically cut the tissue.

It is also envisioned that a substantially dull blade may be utilized with a spring loaded cutting mechanism which, due to the clamping pressure between the opposing jaw members 62 and 64 and due to the force at which the spring-loaded cutting mechanism advances the cutting blade, the tissue will sever along the tissue seal.

In one embodiment, a sealing and cutting mechanism is utilized which is selectively attachable to a conventional forceps. In other words, the sealing and cutting mechanism is disposable and the shaft members 12 and 20 are reposable. The disposable sealing and cutting mechanism along with their respective electrosurgical elements simply mount atop one or both shafts of a conventional forceps to enable the surgeon to seal and cut tissue. Once the surgeon is finished with the operation, the sealing and cutting mechanism is simply detached and discarded.

In one embodiment, a flexible blade may be used with a one or more of the above cutting mechanisms to advance through a curved knife channel. For example, upon distal advancement of the cutting mechanism, the cutting blade will simply flex and ride around the knife channel through the tissue held between jaw members. Alternatively, a curved blade may be utilized which has a similar radius of curvature as the knife channel such that the blade will travel through the knife slot without contacting the surfaces of the knife channel.

It is also contemplated that the blade 90 and blade slot 730 (See FIG. 6E) may be positioned in offset relation to the pivot 165 to facilitate manufacturing and assembly of the forceps 10. In other words, the pivot 165 is radially or laterally offset from the longitudinal axis "A" disposed through the forceps 10. In this embodiment, the offset configuration of the pivot 165 enables the blade 90 to be manufactured in a generally straight configuration which does not interfere with the pivot 165 during distal activation thereof. Likewise, the blade slot 730 may be configured generally straight as well.

It is also contemplated that the forceps may include a safety blade return mechanism (not shown). For example and as mentioned above, the cutting blade 90 may include one or more springs which automatically return the cutting blade after actuation of the actuator. In addition, a manual return may be included which allows the user to manually return the blade 90 if the automatic blade return (e.g., spring) should fail due to sticking, skewing, or some other unforeseen surgical condition. For example, a second pulley (not shown) may be employed opposite the actuating mechanism 40 which allows the user to manually retract the blade 90 should an automatic return (spring) fail. As can be appreciated, this second pulley (or series of pulleys if needed) would be connected to the cutting blade 90 and would operate to facilitate manual retraction as needed during the operation.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An open electrosurgical forceps for sealing tissue, comprising:
   a pair of first and second shaft members each having a jaw member disposed at a distal end thereof, the shaft members movable relative to each other to move the jaw members about a pivot from a first position in spaced relation relative to one another to at least one subsequent position wherein the jaw members cooperate to grasp tissue therebetween;
   each of said jaw members including an electrically conductive sealing surface for communicating electrosurgical energy through tissue held therebetween;
   at least one of the jaw members including a cutting slot defined along a length thereof, the cutting slot configured to accommodate reciprocation of a cutting instrument therethrough;
   an actuator operably coupled to one of the first and second shaft members for selectively advancing the cutting instrument from a first position wherein the cutting instrument is disposed proximal to tissue held between the jaw members to at least one subsequent position wherein the cutting instrument is disposed distal to tissue held between the jaw members,
   wherein upon movement of the jaw members to the at least one subsequent position to grasp tissue therebetween, the shaft members are further moveable toward each other to at least one of a plurality of positions corresponding to a specific closing force between the jaw members; and
   a lockout formed on a part of at least one of the jaw members, the lockout configured to engage the cutting instrument to prevent advancement of the cutting instrument through tissue.

2. An open forceps according to claim 1, wherein the lockout is formed on the pivot, the cutting instrument configured to engage the pivot when the jaw members are in the open position to prevent advancement of the cutting instrument through tissue.

3. An open forceps according to claim 2, wherein the pivot includes a detent disposed thereon configured to engage a corresponding notch disposed in the cutting instrument when the jaw members are in the open position to prevent advancement of the cutting instrument through tissue.

4. An open forceps according to claim 2, wherein the cutting instrument is configured to disengage the pivot when the jaw members are in the at least one subsequent position to permit advancement of the cutting instrument through tissue.

5. An open forceps according to claim 1, wherein the cutting instrument is advanced from the first position to the at least one subsequent position at an angle relative to a longitudinal axis defined by at least one of the shaft members.

6. An open forceps according to claim 1, wherein the plurality of positions are successive positions that increase a closure pressure between the electrically conductive sealing surfaces.

7. An open forceps according to claim 1, wherein each shaft member includes a ratchet interface disposed thereon that cooperates with a corresponding ratchet interface of the opposing shaft member to interlock the shaft members at the at least one position upon movement of the shaft members toward each other.

8. An open forceps according to claim 7, wherein the ratchet interfaces abut one another upon movement of the jaw members to the at least one subsequent position.

9. An open forceps according to claim 7, wherein each ratchet includes a plurality of flanges projecting from inner facing surface thereof that cooperate to interlock the shaft members in the at least one position.

10. An open forceps according to claim 1, wherein at least one of the shaft members includes a visual indicator corresponding to the specific closing force between the jaw members.

11. An open forceps according to claim 1, wherein the at least one position of the shaft members corresponds to a specific strain energy in the shaft members that corresponds to the specific closing force between the jaw members.

12. An open forceps according to claim 1, wherein at least one of the shaft members is resiliently deformable to enable movement of the shaft members toward each other to the at least one of the plurality of positions corresponding to a specific closing force between the jaw members.

13. An open forceps according to claim 1, wherein a spring constant of at least one of the shaft members enables movement of the shaft members toward each other to the at least one of a plurality of positions corresponding to a specific closing force between the jaw members.

14. An open electrosurgical forceps for sealing tissue, comprising:
- a pair of first and second shaft members each having a jaw member disposed at a distal end thereof, the shaft members movable relative to each other to move the jaw members about a pivot from a first position in spaced relation relative to one another to at least one subsequent position wherein the jaw members cooperate to grasp tissue therebetween;
- each of said jaw members including an electrically conductive sealing surface for communicating electrosurgical energy through tissue held therebetween;
- at least one of the jaw members including a cutting slot defined along a length thereof, the cutting slot configured to accommodate reciprocation of a cutting instrument therethrough;
- an actuator operably coupled to one of the first and second shaft members for selectively advancing the cutting instrument from a first position wherein the cutting instrument is disposed proximal to tissue held between the jaw members to at least one subsequent position wherein the cutting instrument is disposed distal to tissue held between the jaw members,
- wherein upon movement of the jaw members to the at least one subsequent position to grasp tissue therebetween, the shaft members are further moveable toward each other to at least one of a plurality of positions corresponding to a specific closing force between the jaw members; and
- a lockout operably coupled to the cutting instrument and forming part of the pivot, wherein the cutting instrument operably engages the pivot when the jaw members are in the open position to prevent advancement of the cutting instrument through tissue.

15. An open forceps according to claim 14, wherein the pivot includes a detent disposed thereon configured to engage a corresponding notch disposed in the cutting instrument when the jaw members are in the open position to prevent advancement of the cutting instrument through tissue.

16. An open forceps according to claim 14, wherein the cutting instrument operably disengages the pivot when the jaw members are in the at least one subsequent position to permit advancement of the cutting instrument through tissue.

17. An open forceps according to claim 14, wherein the cutting instrument is advanced from the first position to the at least one subsequent position at an angle relative to a longitudinal axis defined by at least one of the shaft members.

18. An open electrosurgical forceps for sealing tissue, comprising:
- a pair of first and second shaft members each having a jaw member disposed at a distal end thereof, the shaft members movable relative to each other to move the jaw members about a pivot from a first position in spaced relation relative to one another to at least one subsequent position wherein the jaw members cooperate to grasp tissue therebetween, wherein upon movement of the jaw members to the at least one subsequent position to grasp tissue therebetween, the shaft members are further moveable toward each other to at least one of a plurality of positions corresponding to a specific closing force between the jaw members;
- each of said jaw members including an electrically conductive sealing surface for communicating electrosurgical energy through tissue held therebetween;
- at least one of the jaw members including a cutting slot defined along a length thereof, the cutting slot configured to accommodate reciprocation of a cutting instrument therethrough, the cutting instrument configured to engage at least a portion of the pivot to inhibit reciprocation of the cutting instrument through the cutting slot;
- an actuator operably coupled to one of the first and second shaft members for selectively advancing the cutting instrument from a first position wherein the cutting instrument is disposed proximal to tissue held between the jaw members to at least one subsequent position wherein the cutting instrument is disposed distal to tissue held between the jaw members, wherein the cutting instrument is advanced from the first position to the at least one subsequent position at an angle relative to a longitudinal axis defined by at least one of the shaft members.

* * * * *